(12) United States Patent
Kitano et al.

(10) Patent No.: US 8,903,048 B2
(45) Date of Patent: Dec. 2, 2014

(54) RADIOGRAPHIC IMAGING APPARATUS AND CONTROL METHOD FOR THE SAME

(71) Applicant: FUJIFILM Corporation, Tokyo (JP)

(72) Inventors: Kouichi Kitano, Ashigarakami-gun (JP); Naoyuki Nishino, Ashigarakami-gun (JP); Yasunori Ohta, Ashigarakami-gun (JP); Naoto Iwakiri, Ashigarakami-gun (JP); Haruyasu Nakatsugawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/080,575

(22) Filed: Nov. 14, 2013

(65) Prior Publication Data

US 2014/0072103 A1 Mar. 13, 2014

Related U.S. Application Data

(63) Continuation of application No. PCT/JP2012/068672, filed on Jul. 24, 2012.

(30) Foreign Application Priority Data

Jul. 26, 2011 (JP) .................... 2011-163195

(51) Int. Cl.
*A61B 6/00* (2006.01)
*A61B 8/00* (2006.01)

(52) U.S. Cl.
CPC ............... *A61B 6/542* (2013.01); *A61B 6/4233* (2013.01); *A61B 6/4283* (2013.01); *A61B 6/56* (2013.01); *A61B 8/54* (2013.01)
USPC .......................................... 378/115; 378/116

(58) Field of Classification Search
USPC ................. 378/114–116, 108, 110, 112, 97
See application file for complete search history.

(56) References Cited

U.S. PATENT DOCUMENTS

| | | | |
|---|---|---|---|
| 6,967,332 B2 | 11/2005 | Kobayashi et al. | |
| 7,235,789 B2 | 6/2007 | Kobayashi et al. | |
| 7,507,970 B2 | 3/2009 | Kobayashi et al. | |
| 2007/0297569 A1* | 12/2007 | Saunders | 378/108 |
| 2009/0129546 A1 | 5/2009 | Newman et al. | |
| 2011/0249799 A1* | 10/2011 | Lalena et al. | 378/97 |

FOREIGN PATENT DOCUMENTS

| | | | |
|---|---|---|---|
| JP | 2004-130058 A | 4/2004 | |
| JP | 2008-132216 A | 6/2008 | |
| JP | 2010-213917 A | 9/2010 | |
| JP | 2011-502699 A | 1/2011 | |

OTHER PUBLICATIONS

International Preliminary Report on Patentability and English translation of the Written Opinion of the International Searching Authority for Application No. PCT/JP2012/068672 dated Feb. 6, 2014 (Forms PCT/IB/338, PCT/IB/373, and PCT/ISA/237).
International Search Report issued in PCT/JP2012/068672, dated Aug. 28, 2012.

* cited by examiner

*Primary Examiner* — Hoon Song
(74) *Attorney, Agent, or Firm* — Birch, Stewart, Kolasch & Birch, LLP

(57) ABSTRACT

An X-ray imaging apparatus includes an FPD and short-circuited pixels. The FPD has pixels arranged in arrays for detecting an X-ray image. The short-circuited pixels detect a radiation dose of X-rays in the FPD. The X-ray imaging apparatus is changed over between first and second operating modes. The first operating mode is selected in case of combining with an X-ray generating apparatus with communication compatibility, and performs an exposure control for controlling a total radiation dose according to a detection signal from the short-circuited pixels. The second operating mode is selected in case of combining with an X-ray generating apparatus with communication incompatibility, and performs control of start synchronization for synchronizing operation of the FPD with the emission start of X-rays according to a detection signal from the short-circuited pixels. Thus, control of the X-ray imaging apparatus is changed over appropriately.

20 Claims, 12 Drawing Sheets

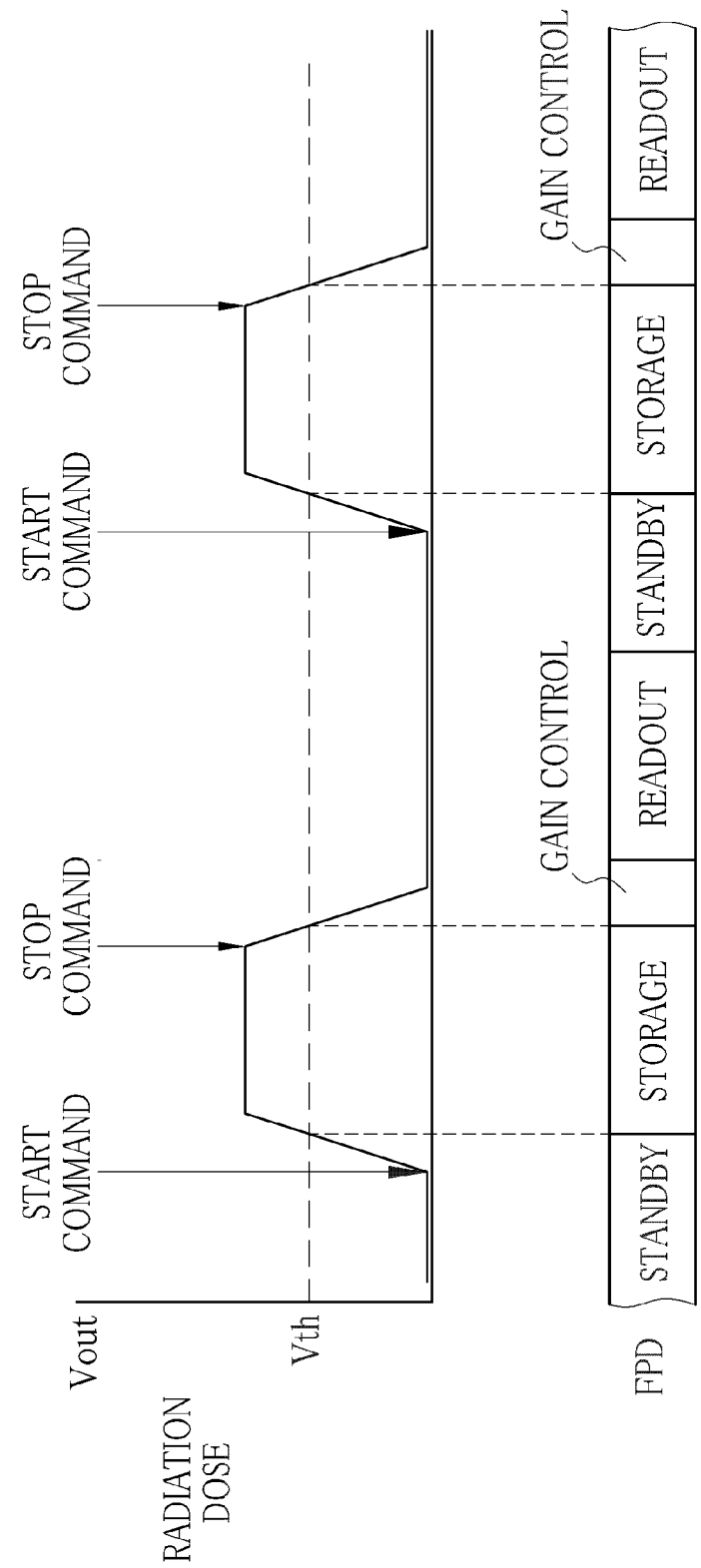

US 8,903,048 B2

RADIOGRAPHIC IMAGING APPARATUS AND CONTROL METHOD FOR THE SAME

CROSS REFERENCE TO RELATED APPLICATIONS

This application is a Continuation of PCT International Application No. PCT/JP2012/068672 filed on Jul. 24, 2012, which claims priority under 35 U.S.C. §119(a) to Patent Application No. 2011-163195 filed in Japan on Jul. 26, 2011, all of which are hereby expressly incorporated by reference into the present application.

BACKGROUND OF THE INVENTION

1. Field of the Invention

The present invention relates to a radiographic imaging apparatus for detecting a radiation image of an object, and a control method for the radiographic imaging apparatus.

2. Description Related to the Prior Art

An X-ray imaging system is known in a medical field in use of radiation, such as X-rays. The X-ray imaging system includes an X-ray generating apparatus and an X-ray imaging apparatus. The X-ray generating apparatus has an X-ray source for generating X-rays. The X-ray imaging apparatus detects an X-ray image of image information of an object by receiving X-rays transmitted through the object after emission from the X-ray source. The X-ray source is provided with an imaging condition inclusive of a tube current and a tube voltage, the tube current determining a dose of X-rays per unit time, the tube voltage determining energy spectrum of X-rays. The imaging condition is determined for each event of imaging according to a body part, age and the like of the object or a body of examination with X-rays. The X-ray source emits X-rays according to the imaging condition.

A newly suggested type of the X-ray imaging apparatus includes an FPD (flat panel detector) or image detector in place of X-ray film or imaging plate (IP) used conventionally (See U.S. Pat. Nos. 6,967,332, 7,235,789 and 7,507,970 (corresponding to JP-A 2004-130058)). The FPD includes a detection panel and a signal processing circuit. The detection panel has an imaging area including plural pixels and signal lines. The pixels store a signal charge according to a radiation dose of X-rays. The signal lines read the signal charge in connection with the pixels. The signal processing circuit reads the stored signal charge form the pixels as a voltage signal, and converts the voltage signal into image data of a digital form. Thus, the X-ray image can be viewed immediately after the imaging in the X-ray imaging apparatus including the FPD.

In the detection panel, each of pixels in the imaging area is constituted by a photo diode as a photoelectric conversion element, and a TFT (thin film transistor). Scintillator (phosphor) is provided in the imaging area for converting X-rays into visible light. The TFT is a switching element for turning on and off electric connection between the photo diode and a signal line, to change over operation of the pixel. When the TFT is turned off, a non-conductive state is created between the photo diode and the signal line, to start a storage step in which a signal charge is stored in the photo diode. When the TFT is turned on, a conductive state is created between the photo diode and the signal line, to start a readout step in which the signal charge is read from the photo diode through the TFT and the signal line.

It is necessary with the X-ray imaging apparatus having the FPD to perform control of start synchronization to start the storage step in synchronism with the emission start of X-rays, unlike the X-ray film or imaging plate (IP). A widely used example of the control of start synchronization is a signal communication method in which a sync signal is sent between the X-ray generating apparatus and the X-ray imaging apparatus.

Examples of the control of start synchronization include not only the signal communication method but an auto-detecting method disclosed in U.S. Pat. Nos. 6,967,332, 7,235,789 and 7,507,970. In the auto-detecting method, changes in the radiation dose of X-rays emitted by the X-ray generating apparatus are monitored in the X-ray imaging apparatus, to detect a time point of an emission start of X-rays in a manner of auto-detection. The X-ray imaging apparatus disclosed in U.S. Pat. Nos. 6,967,332, 7,235,789 and 7,507,970 includes detecting elements, disposed in addition to normal pixels in the imaging area of the FPD, for detecting the radiation dose of radiation to check a time point of the emission start of X-rays. The control of start synchronization is performed by use of the detecting elements in the auto-detecting method. It is possible in the auto-detecting method to perform the control of start synchronization without transmission of a sync signal between the X-ray generating apparatus and the X-ray imaging apparatus.

Also, U.S. Pat. Nos. 6,967,332, 7,235,789 and 7,507,970 disclose the use of the detecting elements for AEC or automatic exposure control instead of the use for the control of start synchronization.

In the AEC, a total radiation dose of X-rays received from the X-ray generating apparatus is measured by the X-ray imaging apparatus. The AEC is a control of an exposure of the X-ray image by stopping emission of X-rays according to sending of a stop signal to the X-ray generating apparatus upon reach of the total radiation dose to a predetermined threshold. The AEC is performed for suitably controlling the total radiation dose of X-rays. The AEC makes it possible to prevent drop of image quality as an optimum exposure is ensured. Also, overexposure to the object can be prevented. Even in use of the X-ray film or imaging plate (IP) distinct from the FPD, the AEC has been performed in the prior art by combining the X-ray film or imaging plate (IP) with an exposure control device referred to as a photo timer. As disclosed in U.S. Pat. Nos. 6,967,332, 7,235,789 and 7,507,970, the detecting elements in the FPD are used for the AEC to make a special exposure control device unnecessary in a form discrete from the FPD.

JP-A 2008-132216 discloses the X-ray imaging apparatus in which the signal communication method and the auto-detecting method of JP-A 2008-132216 can be used as methods for the control of start synchronization. The X-ray imaging apparatus of JP-A 2008-132216 includes a wireless communication function for wirelessly transmitting a sync signal in cooperation with the X-ray generating apparatus. In a normal situation, the control of start synchronization is performed in the signal communication method. If a communication state of the wireless communication becomes poor, or if failure in the wireless communication occurs, then an emission start of X-rays is detected with the FPD in the auto-detecting method, to perform the control of start synchronization. In short, the X-ray imaging apparatus of JP-A 2008-132216 utilizes the signal communication method for the control of start synchronization normally, but utilizes the auto-detecting method exceptionally in the case of the poor communication state.

In medical facilities with the X-ray imaging system, there has been a recent trend of changing over from a conventional type of the X-ray imaging apparatus with the X-ray film or imaging plate (IP) to a new type of the X-ray imaging apparatus with the FPD. However, the entirety of the X-ray imaging system is remarkably expensive. A cost of updating is seriously high if the X-ray imaging system inclusive of the X-ray generating apparatus is totally updated. Thus, there is an idea of paying for introducing only the X-ray imaging apparatus with the FPD, and combining this with the existing type of the X-ray generating apparatus to update the X-ray imaging system.

As described heretofore, the control of start synchronization is required between the X-ray imaging apparatus and the X-ray generating apparatus to use a new type of the X-ray imaging apparatus having the FPD. A known type of the X-ray generating apparatus has the communication function in connection with the X-ray imaging apparatus, and a communication interface (standards of a cable and connector, signal format, and the like) is compatible with the communication interface of the X-ray imaging apparatus. In the case of this communication compatibility between the X-ray generating apparatus and the X-ray imaging apparatus, it is possible to perform the control of start synchronization in a normal type of the signal communication method.

In general, the signal communication method is more normally used than the auto-detecting method, and is more reliable than the latter as a method of the control of start synchronization. In the case of communication compatibility with the X-ray generating apparatus, it is preferable to perform the control of start synchronization of the signal communication method in the X-ray imaging apparatus.

However, it is likely that the X-ray generating apparatus of the existing type does not have the communication function for communicating with the X-ray imaging apparatus. Even if the communication function exists, communication incompatibility is likely to occur between the communication interface of the X-ray generating apparatus and that of the X-ray imaging apparatus. Communication is impossible between the X-ray generating apparatus and the X-ray imaging apparatus, in which the control of start synchronization according to the signal communication method cannot be performed.

For this situation, the X-ray imaging apparatus in which the control of start synchronization of the auto-detecting method is possible according to U.S. Pat. Nos. 6,967,332, 7,235,789 and 7,507,970 and JP-A 2008-132216 can be used, so as to establish the X-ray imaging system in combination of the X-ray generating apparatus of a conventional type.

The AEC is a control on a condition of stopping emission of X-rays by sending a stop signal from the X-ray imaging apparatus to the X-ray generating apparatus. As emission of X-rays cannot be stopped in the case of impossibility of communication with the X-ray generating apparatus, effect of ensuring an optimum exposure of the X-ray image, effect of overexposure to the object, and other effect of the AEC cannot be obtained. Specifically, if the AEC is performed in the X-ray imaging apparatus without communicability with the X-ray generating apparatus, no stop of emission of X-rays occurs, because the X-ray generating apparatus cannot receive a stop signal even upon outputting the stop signal from the X-ray imaging apparatus. On the other hand, it is likely in the X-ray imaging apparatus that the readout step is started after the storage step on a condition of stopping emission of X-rays with the AEC. As the emission of X-rays continues even during the readout step, noise may be caused to lower image quality of the X-ray image. Also, X-rays continue being applied even after the end of the storage step. X-rays not contributing to the X-ray image are emitted. Thus, no effect of preventing overexposing the object can be obtained.

Consequently, the combined use of the X-ray imaging apparatus with the X-ray generating apparatus can be made appropriate in relation to the control of start synchronization and the AEC of the X-ray imaging apparatus according to communication compatibility or incompatibility with the X-ray generating apparatus.

Although U.S. Pat. Nos. 6,967,332, 7,235,789 and 7,507,970 disclose both of the control of start synchronization and the AEC for the auto-detecting method by use of the detecting elements of the FPD, there is no disclosure as to which of the control of start synchronization and the AEC should be performed by use of the detecting elements.

Although JP-A 2008-132216 discloses the signal communication method and the auto-detecting method in relation to the control of start synchronization, there is no suggestion of the AEC.

SUMMARY OF THE INVENTION

In view of the foregoing problems, an object of the present invention is to provide a radiographic imaging apparatus in which control can be performed suitably according to communication compatibility or incompatibility with the X-ray generating apparatus in relation to the control of start synchronization and the AEC (automatic exposure control), and a control method for the radiographic imaging apparatus.

In order to achieve the above and other objects and advantages of this invention, a radiographic imaging apparatus for use with a radiation generating apparatus for emitting radiation is provided. An image detector has an imaging area in which plural pixels are arranged in arrays for storing a signal charge according to a radiation dose of the radiation upon receiving the radiation from the radiation generating apparatus, for detecting a radiation image by receiving radiation transmitted through an object. A radiation detector outputs a detection signal according to the radiation dose, in order to detect an emission start of the radiation from the radiation generating apparatus, and/or in order to measure a total radiation dose of the radiation. A communication interface communicates with the radiation generating apparatus. A mode selector selectively sets one of first and second operating modes. The first operating mode is used in case of combination with the radiation generating apparatus with which the communication interface has communication compatibility, for performing at least an exposure control for measuring the total radiation dose according to the detection signal from the radiation detector. The second operating mode is used in case of combination with the radiation generating apparatus with which the communication interface has communication incompatibility, for performing at least a control of start synchronization for detecting the emission start according to the detection signal from the radiation detector and starting a storage step of storing the signal charge of the image detector in synchronism with the emission start. A controller controls the image detector according to the one operating mode selectively set by the mode selector.

In the first operating mode, the controller starts the storage step in synchronism with an emission start signal transmitted to the communication interface by the radiation generating apparatus.

In the first operating mode, the controller measures the total radiation dose by accumulating the detection signal from the radiation detector, and when the total radiation dose reaches a threshold, causes the communication interface to transmit a stop signal to the radiation generating apparatus to stop emission of the radiation.

When the total radiation dose reaches the threshold, the controller terminates the storage step of the image detector.

In another preferred embodiment, in the second operating mode, the controller detects an emission end of the radiation from the radiation generating apparatus according to the detection signal from the radiation detector in addition to the control of the start synchronization, and terminates the storage step of the image detector in synchronism with the emission end.

In one preferred embodiment, in the second operating mode, the controller terminates the storage step upon a lapse of a predetermined time after a start of the storage step.

In still another preferred embodiment, in the first and second operating modes, the controller carries out resetting in which a signal charge of the pixels is reset after detecting the emission start and before starting the storage step.

In one preferred embodiment, in the first operating mode, the controller performs the control of the start synchronization in addition to the exposure control.

In another preferred embodiment, the mode selector selects the operating modes according to manual operation for mode selection.

In one preferred embodiment, the mode selector detects communication compatibility or incompatibility with the radiation generating apparatus, and automatically selects the operating modes according to a result of detection.

Furthermore, a notifier for notifying information as to which of the first and second operating modes is selected.

In the first operating mode, the emission start signal from the radiation generating apparatus is constituted by a pulse wave, and the communication interface notifies the controller of receiving the emission start signal upon detecting an edge of the pulse wave.

The radiation detector is disposed in the imaging area.

The radiation detector is disposed in each one of plural partial areas defined by splitting the imaging area. The controller changes over the partial areas for use between the exposure control and the control of the start synchronization.

The plural partial areas include a central partial area disposed at a center of the imaging area and a side partial area disposed in a periphery of the central partial area. The controller uses the central and side partial areas selectively in the exposure control and the control of the start synchronization.

The controller changes a sensitivity of the radiation detector in the partial areas for use in respectively the exposure control and the control of the start synchronization.

The radiation detector is a short-circuited pixel where one of the pixels is always short-circuited with a signal line for reading out the signal charge from the pixel, for outputting the signal charge to the signal line according to the radiation dose.

The image detector operates for motion imaging by receiving plural radiation pulses of the radiation emitted successively by the radiation generating apparatus. In the motion imaging, the controller detects an edge of the radiation pulses according to the detection signal from the radiation detector, and synchronizes the storage step of the image detector with emission of the radiation pulses.

The controller measures the radiation dose per the radiation pulses according to the detection signal from the radiation detector, and controls an output gain of the signal charge according to a result of measurement.

Also, a control method for a radiographic imaging apparatus for use with a radiation generating apparatus for emitting radiation is provided, the radiographic imaging apparatus including an image detector, having an imaging area in which plural pixels are arranged in arrays for storing a signal charge according to a radiation dose of the radiation upon receiving the radiation from the radiation generating apparatus, for detecting a radiation image by receiving radiation transmitted through an object, a radiation detector for outputting a detection signal according to the radiation dose, in order to detect an emission start of the radiation from the radiation generating apparatus, and/or in order to measure a total radiation dose of the radiation, and a communication interface for communicating with the radiation generating apparatus. The control method includes a step of selectively setting one of first and second operating modes. The first operating mode is used in case of combination with the radiation generating apparatus with which the communication interface has communication compatibility, for performing at least an exposure control for measuring the total radiation dose according to the detection signal from the radiation detector. The second operating mode is used in case of combination with the radiation generating apparatus with which the communication interface has communication incompatibility, for performing at least a control of start synchronization for detecting the emission start according to the detection signal from the radiation detector and starting a storage step of storing the signal charge of the image detector in synchronism with the emission start. The image detector and the radiation detector are controlled according to the one operating mode selectively set by the mode setting step.

In the present invention, control can be performed suitably according to communication compatibility or incompatibility with the X-ray generating apparatus in relation to the control of start synchronization and the AEC (automatic exposure control).

BRIEF DESCRIPTION OF THE DRAWINGS

The above objects and advantages of the present invention will become more apparent from the following detailed description when read in connection with the accompanying drawings, in which:

FIG. 15 is an explanatory view illustrating steps of motion imaging of a fifth embodiment.

DETAILED DESCRIPTION OF THE PREFERRED EMBODIMENT(S) OF THE PRESENT INVENTION

[First Embodiment]

Figure 1:
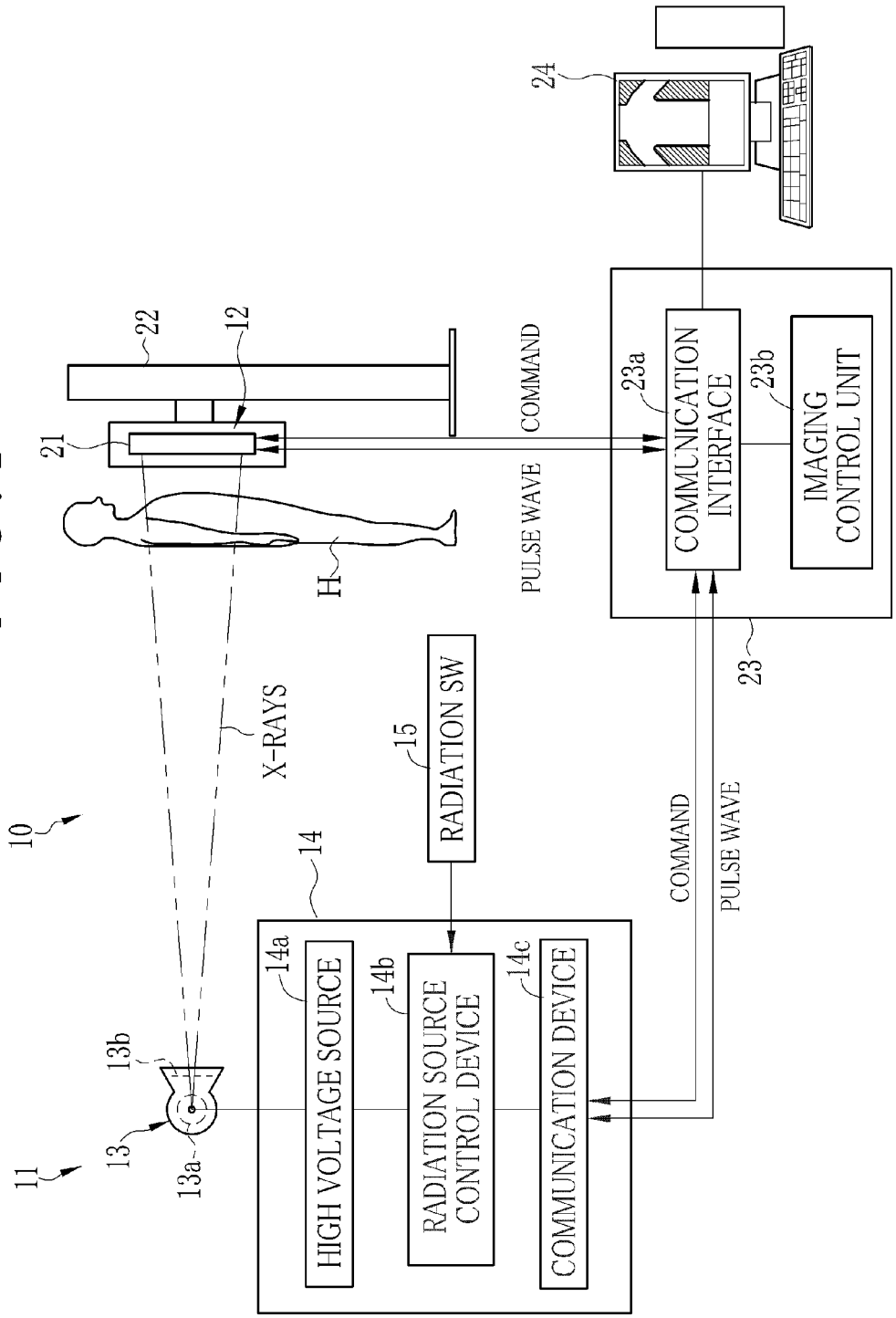
FIG. 1 is an explanatory view schematically illustrating an X-ray imaging system having an X-ray generating apparatus having communication compatibility with an X-ray imaging apparatus.

In FIG. 1, an X-ray imaging system 10 is constituted by assembling an X-ray imaging apparatus 12 in an X-ray imaging system, which is conventional and has an X-ray generating apparatus 11 and an imaging stand 22. The X-ray generating apparatus 11 is communicable with an external device. The imaging stand 22 is so formed that a film cassette or IP cassette can be mounted thereon. The X-ray imaging apparatus 12 includes an X-ray imaging assembly 21 (imaging device), a controller 23 (imaging controller) and a console unit 24.

The X-ray generating apparatus 11 includes an X-ray source 13, a radiation source control assembly 14 (control unit) and a radiation switch 15. The radiation source control assembly 14 controls the X-ray source 13. The X-ray source 13 includes an X-ray tube 13a and a radiation field limiting device (collimator) 13b. The X-ray tube 13a emits X-rays. The radiation field limiting device 13b limits an irradiation field of X-rays emitted by the X-ray tube 13a.

The X-ray tube 13a has a cathode and an anode (target), the cathode having filaments for emitting thermal electrons, the anode undergoing collision of the thermal electrons from the cathode to emit X-rays. The radiation field limiting device 13b includes four metal lead plates, which shield X-rays, are arranged in a frame form, and have an emitting opening for passing X-rays. The metal lead plates are shifted to change the sizes of the emitting opening to limit the radiation field. The four metal lead plates are combined in two pairs. Metal lead plates in each of the pairs are opposed to one another. The pairs are arranged in two directions perpendicular with one another to define the quadrilateral emitting opening.

The radiation source control assembly 14 includes a high voltage source 14a, a radiation source control device 14b and a communication device 14c. The high voltage source 14a supplies the X-ray source 13 with high voltage. The radiation source control device 14b controls a tube voltage, tube current and irradiation time of X-rays. The tube voltage is a value for determining energy spectrum or quality of X-rays emitted by the X-ray source 13. The tube current is a value for determining a radiation dose per unit time. The communication device 14c is communicable with the controller 23 in a wired manner or wirelessly. The high voltage source 14a boosts an input voltage with a transformer, generates the tube voltage as a high voltage, and supplies the X-ray source 13 with drive power by use of a high voltage cable. An imaging condition including the tube voltage, tube current and emission stop condition is manually set in the radiation source control device 14b by a radiology technician or operator with an input panel of the radiation source control assembly 14.

The radiation switch 15 is connected to the radiation source control assembly 14 by a signal cable. The radiation switch 15 is a two-step switch operable by the radiology technician, generates a warmup start signal for starting warming up the X-ray source 13 upon a first step of depression, and generates an emission start signal for the X-ray source 13 upon a second step of depression. Those signals are input to the radiation source control assembly 14 by a signal cable.

The radiation source control device 14b controls operation of the X-ray source 13 according to a control signal from the radiation switch 15. Upon receiving an emission start signal from the radiation switch 15, the radiation source control assembly 14 instructs the X-ray source 13 to start, and starts supplying power. Thus, the X-ray source 13 starts emission. Upon starting the supply of power, the radiation source control device 14b causes the communication device 14c to send an emission start signal to the controller 23 as a sync signal expressing an emission start of X-rays. The emission start signal is used for a control of start synchronization for synchronizing operation of the X-ray imaging assembly 21 with a time point of the emission start of X-rays from the X-ray generating apparatus 11.

If the irradiation time is specified as an emission stop condition set according to the imaging condition, the radiation source control device 14b operates a timer upon starting the power supply, and starts measuring the irradiation time of X-rays. When the irradiation time set according to the imaging condition elapses, the radiation source control device 14b sends a stop command to the X-ray source 13 to stop the power supply. The X-ray source 13 stops the emission of X-rays upon receiving the stop command. If priority to a stop signal from an external device is specified as an emission stop condition set according to the imaging condition, the radiation source control device 14b outputs a stop command upon inputting the stop signal from the controller 23 to the communication device 14c, to stop the power supply.

The imaging stand 22 has a slot in which a film cassette or IP cassette is mounted removably, and is so positioned that its receiving surface for receiving X-rays is opposed to the X-ray source 13. Note that the example of the imaging stand 22 is a stand where the object H is imaged in an erect orientation. However, a table on which the object H is laid horizontally may be used in place of the imaging stand 22.

The X-ray imaging apparatus 12 is constituted by the X-ray imaging assembly 21, the controller 23 and the console unit 24. The X-ray imaging assembly 21 includes a flat panel detector 36 (FPD as image detector) (See FIG. 3) and a portable housing for containing the flat panel detector 36, and is a portable type of radiographic imaging assembly for receiving X-rays passed through a body (object) H upon emission from the X-ray source 13, to detect an X-ray image of the body H. The X-ray imaging assembly 21 has the flat housing of which a plane shape is substantially quadrilateral, and has a plane size as large as a film cassette or IP cassette, so that the X-ray imaging assembly 21 is mountable on the imaging stand 22.

The controller 23 includes a communication interface 23a and an imaging control unit 23b. The communication interface 23a communicates with the X-ray generating apparatus 11, the X-ray imaging assembly 21 and the console unit 24 in a wired or wireless manner. The imaging control unit 23b controls the X-ray imaging assembly 21 by use of the communication interface 23a. The imaging control unit 23b transmits information of an imaging condition to the X-ray imaging assembly 21 to condition the signal processing in the flat panel detector 36, and also receives a sync signal from the X-ray generating apparatus 11 to synchronize the emission of the X-ray source 13 with the storage step of the flat panel detector 36. The imaging control unit 23b performs the sync control between the X-ray source 13 and the flat panel detector 36 by sending the sync signal to the X-ray imaging assembly 21. Also, image data output by the X-ray imaging assembly 21 is received by the imaging control unit 23b with the communication interface 23a, and then sent to the console unit 24.

The console unit 24 receives information of an examination request of the patient, such as sex, age, body part, purpose of imaging, and the like, and causes the display panel to display the information of the examination request. The examination request information is originally supplied by an outer system for managing patient information or diagnosis information, such as the HIS (Hospital Information System) and RIS (Radiography Information System). Also, the examination request information can be input by an operator or technician manually. He or she observes the examination request information on the display panel, and selectively determines an imaging condition according to the same by viewing images on the console unit 24.

The console unit 24 sends the imaging condition to the controller 23, and processes data of an X-ray image output by the controller 23 in image processing of various functions, such as gamma correction, frequency processing and the like. The X-ray image after the image processing is displayed on a display panel of the console unit 24. The data of the X-ray image is stored in a data storage device, such as a hard disk or memory in the console unit 24, or an image storage server in the network connection with the console unit 24.

Figure 2:
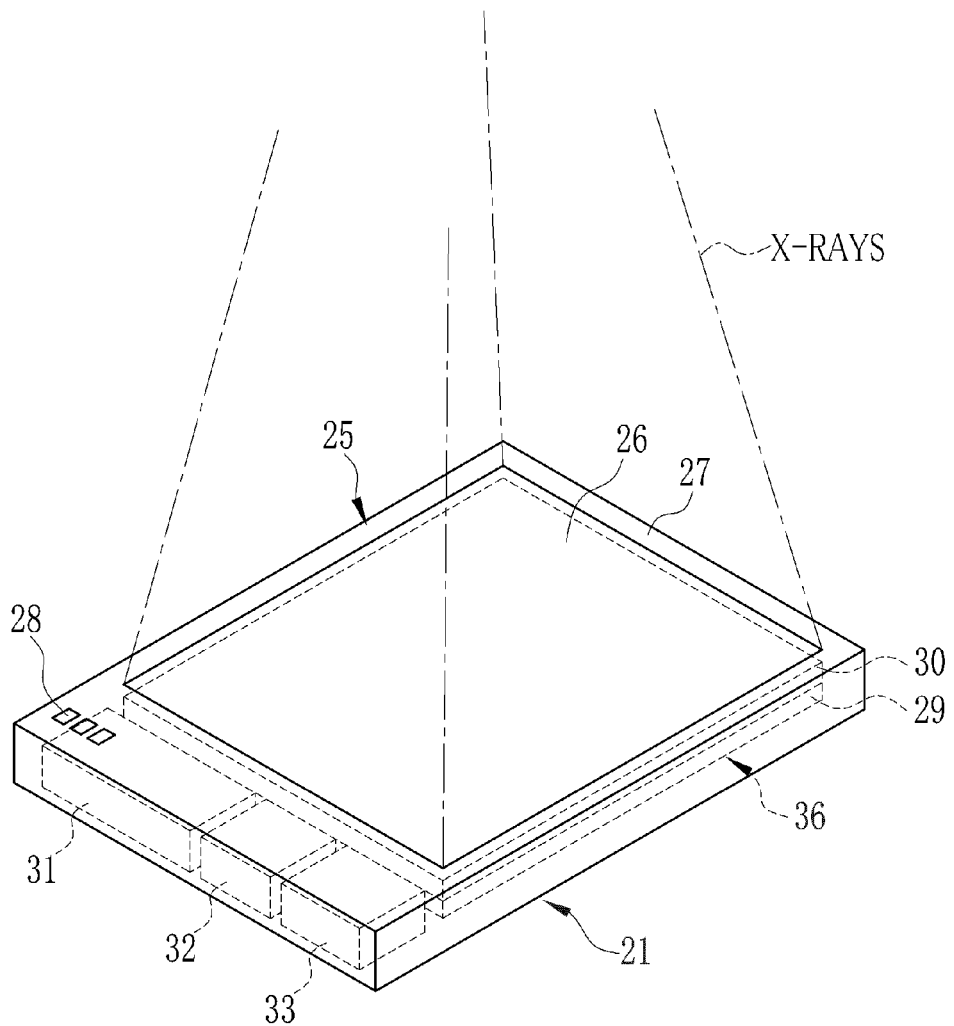
FIG. 2 is a perspective view of appearance illustrating the X-ray imaging apparatus.

As illustrated in FIG. 2, the X-ray imaging assembly 21 has a housing 25 of which a quadrilateral upper surface is a receiving surface of radiation. The housing 25 includes a top panel 26 with the receiving surface and a housing shell 27 for constituting elements other than the top panel 26. For example, the top panel 26 is constituted by carbon and the like. The housing shell 27 is constituted by metal, resin and the like. Therefore, absorption of X-rays with the top panel 26 is suppressed. Strength of the housing shell 27 is ensured.

An indicator 28 is disposed on an upper surface of the housing 25 as a notifier for notifying an operation state of the X-ray imaging assembly 21 and the like. The indicator 28 includes, for example, a plurality of light emitting devices, and indicates various data by combining illuminating states of the light emitting devices, such as operation states, operating modes, available performance of a battery and the like of the X-ray imaging assembly 21. Examples of the operation states are "ready state" as standby for imaging, and "state during data transmission" for transmitting image data after the imaging. Examples of the operating modes are a "first operating mode" for use in case of combining the X-ray imaging assembly 21 with an X-ray generating apparatus in communication compatibility, and a "second operating mode" for use in case of combining the X-ray imaging assembly 21 with an X-ray generating apparatus in communication incompatibility. The first and second operating modes will be described later in detail. The indicator 28 may be a display device such as an LCD. Note that a function of the indicator 28 may be incorporated in the console unit 24.

The flat panel detector 36 is disposed in the housing 25 of the X-ray imaging assembly 21, opposed to a receiving surface, for detecting an X-ray image as an image detector. The flat panel detector 36 is an indirect conversion type, and includes a scintillator 29 and a detection panel 30. The scintillator 29 converts X-rays into visible light. The detection panel 30 photoelectrically detects the visible light converted by the scintillator 29. The flat panel detector 36 is a type of "Irradiation Side Sampling (ISS)" in which the detection panel 30 is disposed on a side of the scintillator 29 on the receiving surface. Note that the flat panel detector 36 may be a type of "Penetration Side Sampling (PSS)" in which disposition of the scintillator 29 and the detection panel 30 is reversed.

Electronic circuits 31, a battery 32 and a communication interface 33 are disposed in the housing 25 on one end thereof along a transverse direction of the receiving surface. The electronic circuits 31 operate for controlling the flat panel detector 36, and are protected by a material radiopaque to X-rays in order to prevent electronic elements from being damaged with X-rays. The battery 32 is contained in the housing 25 in a chargeable and removable manner, and supplies power to the flat panel detector 36, the electronic circuits 31 and the communication interface 33. The communication interface 33 communicates with the controller 23 in a wired manner or wirelessly.

Figure 3:
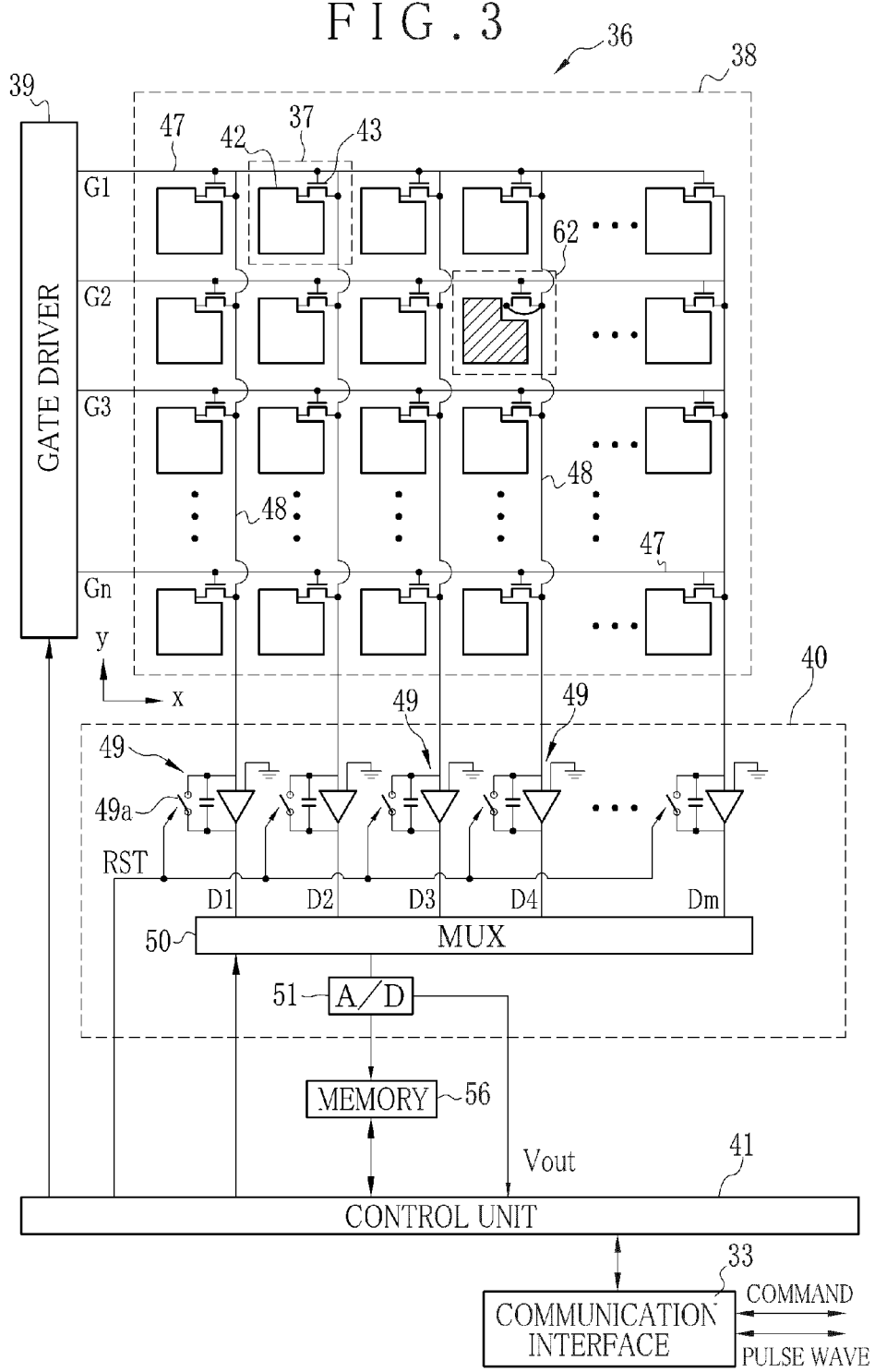
FIG. 3 is an explanatory view illustrating an FPD.

In FIG. 3, the flat panel detector 36 includes the detection panel 30, a gate driver 39, a signal processing circuit 40 and a control unit 41. The signal processing circuit 40 and the control unit 41 constitute the electronic circuits 31. The detection panel 30 has a TFT active matrix substrate, and an imaging area 38 defined on the substrate and constituted by plural pixels 37 for storing a signal charge according to a radiation dose of X-rays. The gate driver 39 drives the pixels 37 and controls the readout step of the signal charge. The signal processing circuit 40 outputs digital data by conversion of the signal charge read from the pixels 37. The control unit 41 controls the gate driver 39 and the signal processing circuit 40 to control operation of the flat panel detector 36. The communication interface 33 is connected to the control unit 41 for communication with the controller 23 in a wired or wireless manner. The pixels 37 are arranged in a matrix form of n arrays (x direction) and m columns (y direction) in a two-dimensional manner at a predetermined pitch.

The flat panel detector 36 has scintillator (not shown) for converting X-rays to visible light, and is an indirect conversion type in which the visible light from the scintillator is photoelectrically converted with the pixels 37. The scintillator is opposed fully to the imaging area 38 where the pixels 37 are arranged. The scintillator is constituted by phosphor formed from cesium iodide (CsI) or GOS (gadolinium oxysulfide). Also, the flat panel detector can be a direct conversion type in which a conversion layer of amorphous selenium and the like directly converts X-rays into electric charge.

Each of the pixels 37 includes a photo diode 42, a capacitor (not shown) and a thin film transistor 43 (TFT) as a switching element. The photo diode 42 is a photoelectric conversion element for generating charge (electron-hole pairs) upon entry of visible light. The capacitor stores the charge generated by the photo diode 42.

The photo diode 42 has a structure including a semiconductor layer such as a-Si (amorphous silicon), for example, of the PIN type, and upper and lower electrodes formed on the semiconductor layer. The TFT 43 is connected to the lower electrode of the photo diode 42. A bias line (not shown) is connected to the upper electrode.

A bias voltage is applied to an upper electrode of the photo diode 42 for all the pixels 37 in the imaging area 38 through a bias line. An electric field is created in the semiconductor layer in the photo diode 42 by the application of the bias voltage. Charge generated in the semiconductor layer by the photoelectric conversion (electron-hole pairs) is moved to the upper and lower electrodes of which one has a positive polarity and the other has a negative polarity. The charge is stored in the capacitor.

The TFTs 43 have electrodes of a gate, source and drain. A scan line 47 is connected with the gate of the TFTs 43. A signal line 48 is connected with the source. Each of the photo diodes 42 is connected with the drain. The scan lines 47 and the signal lines 48 are disposed in a form of a grating. A number of the scan lines 47 is n or the array number of the pixels 37 in the imaging area 38. The scan lines 47 are common lines connected to the pixels 37 of the arrays. A number of the signal lines 48 is m or the column number of the pixels 37. The signal lines 48 are common lines connected to the pixels 37 of the arrays. The scan lines 47 are connected to the gate driver 39. The signal lines 48 are connected to the signal processing circuit 40.

The gate driver 39 drives the TFTs 43 for operation of the storage step, readout step and reset step. In the storage step, a signal charge according to the radiation dose of X-rays is stored in the pixels 37. In the readout step, the signal charge is read from the pixels 37. In the reset step, the charge stored in the pixels 37 is reset. The control unit 41 controls time points of start of the storage step, readout step and reset step carried out by the gate driver 39.

In the storage step, the TFTs 43 are in a turn-off state. During this period, a signal charge is stored in the pixels 37. In the readout step, gate pulses G1-Gn for driving the TFTs 43 of a common array together are generated by the gate driver 39, and activate the scan lines 47 serially one array after another, to turn on the TFTs 43 by one array in connection with the scan lines 47.

When the TFTs 43 of one array come to be in a turn-on state, the signal charge stored in respectively the pixels 37 of the one array is input to the signal processing circuit 40 through the signal lines 48. In the signal processing circuit 40, the signal charge of the one array is converted into voltage and output. An output voltage according to respectively the signal charge is read as voltage signals D1-Dm. The voltage signals D1-Dm of the analog form are converted into digital data so that image data is created as digital pixel values expressing density of respectively the pixels of the one array. The image data is output to a memory 56 contained in the housing of the X-ray imaging assembly 21.

A dark current is generated in the semiconductor layer of the photo diodes 42 irrespective of entry of X-rays. A dark current charge as charge according to the dark current is stored in the capacitor owing to application of the bias voltage. The dark current creates a noise component in the image data. Resetting is carried out for eliminating the dark current. In the resetting, the dark current generated at the pixels 37 is discharged from the pixels 37 through the signal lines 48.

An example of the method of the resetting is sequential resetting in which the pixels 37 are reset by one array. In a manner similar to the readout step of a signal charge, the gate driver 39 successively sends gate pulses G1-Gn to the scan lines 47, and turns on the TFTs 43 of the pixels 37 by one array. While each of the TFTs 43 is turned on, a dark current charge from the pixel 37 flows to the signal processing circuit 40 through the signal line 48.

As a difference of the resetting from the readout step, there is no readout step of an output voltage according to the dark current charge in the signal processing circuit 40. The control unit 41 outputs a reset pulse RST to the signal processing circuit 40 in synchronism with each of the gate pulses G1-Gn. Upon inputting the reset pulse RST to the signal processing circuit 40, reset switches 49a of integrating amplifiers 49 to be described later are turned on, to reset the input dark current charge.

Instead of the sequential resetting, the simultaneous resetting and the total pixel resetting can be used. In the simultaneous resetting, pixels are grouped in plural groups each of which is constituted by a predetermined number of arrays of pixels. Pixels of each of the groups are reset in the sequential resetting, to discharge the dark current charge simultaneously from the arrays of the various groups. In the total pixel resetting, a gate pulse is input for all of the arrays to discharge the dark current charge of all the pixels simultaneously. According to the simultaneous resetting and the total pixel resetting, it is possible to quicken reset operation.

The signal processing circuit 40 includes the integrating amplifiers 49, an MUX 50 (multiplexer) and an A/D converter 51. The integrating amplifiers 49 are connected with the signal lines discretely from one another. Each of the integrating amplifiers 49 includes an operational amplifier, and a capacitor connected between input and output terminals of the operational amplifier. Each of the signal lines 48 is connected with a first one of the input terminals of the operational amplifier. A second one of the input terminals of the integrating amplifier 49 is grounded (GND). The integrating amplifiers 49 accumulate signal charge input by the signal lines 48, and convert the charge into voltage signals D1-Dm as outputs.

Output terminals of the integrating amplifiers 49 of respective columns are connected to the MUX 50 by amplifiers (not shown) and a sample-hold circuit (not shown), the amplifiers amplifying the voltage signals D1-Dm, the sample-hold circuit holding the voltage signals D1-Dm. The MUX 50 selects one of the amplifier integrators 49 from each one of their columns in parallel, so that the voltage signals D1-Dm output by the selected amplifier integrators 49 are input to the A/D converter 51 serially. The A/D converter 51 converts the voltage signals D1-Dm in an analog form to digital pixel values according to their signal level.

In the readout step for the signal charge after the storage step, the TFTs 43 are turned on by gate pulses one array after another. The signal charge stored in capacitors of the pixels 37 of respective columns in the arrays is input to the integrating amplifiers 49 by the signal lines 48.

When the voltage signals D1-Dm of the one array are output by the integrating amplifiers 49, the control unit 41 outputs a reset pulse (reset signal) to the integrating amplifiers 49 and turns on the reset switches 49a of the same. The signal charge of the one array stored in the integrating amplifiers 49 is reset. Upon the resetting, a gate pulse of a succeeding array is output by the gate driver 39, to start reading the signal charge of the pixels 37 of the succeeding array. Those steps are repeated successively to read the signal charge of the pixels 37 of all the arrays.

When the readout step of all the arrays is completed, image data of an X-ray image of one frame is written to the memory 56. The image data written to the memory 56 is processed in image correction, such as offset correction and sensitivity correction. In the offset correction, an offset component is eliminated as a fixed pattern noise created by a specificity and environment of the flat panel detector 36. In the sensitivity correction, errors in the sensitivity of the photo diode 42 of the pixels 37 and errors in the output characteristic are corrected. Image data are read from the memory 56, output to the controller 23, and transmitted to the console unit 24. Thus, the X-ray image of the object H is detected.

In addition to the function of image detection, the flat panel detector 36 has a function of detecting a radiation dose of X-rays emitted by the X-ray source 13 for use in sync control with the X-ray generating apparatus 11 and exposure control of an X-ray image. As hatched in FIG. 3, short-circuited pixels 62 are provided in the imaging area 38 of the flat panel detector 36 as a radiation detector for detecting a radiation dose of X-rays. Although only one of the short-circuited pixels 62 is depicted in FIG. 3, a plurality of the short-circuited pixels 62 are present actually, and disposed on the entirety of the imaging area 38 discretely from one another. The number of the short-circuited pixels 62 is, for example, approximately 1% as high as the number of the pixels 37. Turning on and off of the TFTs 43 causes turning on and off of electrical connection of the pixels 37 with the signal lines 48. In contrast, the short-circuited pixels 62 are always short-circuited with the signal lines 48.

The short-circuited pixels 62 are structurally similar to the pixels 37, and have the photo diode 42 and the TFTs 43. The photo diode 42 generates a signal charge according to a radiation dose of X-rays. A structural difference of the short-circuited pixels 62 from the pixels 37 is a short-circuited form between the source and drain of the TFTs 43 by wiring. A switching function of the TFTs 43 of the short-circuited pixels 62 is suppressed. Thus, the signal charge generated by the photo diode 42 of the short-circuited pixels 62 always flows to the signal lines 48, and is input to the integrating amplifiers 49. Note that it is possible directly to connect the photo diode 42 to the signal lines 48 without providing the TFTs 43 at the short-circuited pixels 62 and instead of wiring between the source and drain of the TFTs 43 of the short-circuited pixels 62.

The control unit 41 measures a radiation dose of X-rays applied by the X-ray source 13 to the flat panel detector 36 according to an output of the short-circuited pixels 62. The control unit 41 selects one of the integrating amplifiers 49 to which a signal charge is input from the short-circuited pixels 62 by use of the MUX 50, and reads a voltage signal of the integrating amplifiers 49 as an output voltage Vout of the short-circuited pixels 62. The control unit 41 resets the integrating amplifiers 49 upon reading the output voltage Vout at one time. During the storage step, the control unit 41 repeats the readout step of the output voltage Vout at a very short period relative to irradiation time of X-rays, so as to monitor changes in the intensity of X-rays being applied.

The control unit 41 converts the value of the output voltage Vout into digital data, and writes the same to the memory 56. The control unit 41 monitors a change in a radiation dose of X-rays emitted by the X-ray source 13 according to a change with time in the output voltage Vout stored in the memory 56, and can detect time points of the emission start and emission end of X-rays from the X-ray generating apparatus 11.

Also, the control unit 41 can measure a total radiation dose of X-rays applied by the X-ray source 13 to the flat panel detector 36 according to an output of the short-circuited pixels 62. After starting emission of X-rays, the control unit 41 reads the output voltage Vout of the short-circuited pixels 62 at a short interval in a manner similar to the above-described detection of the time point of the emission start, and measures the total radiation dose of X-rays by accumulating the output voltage Vout.

Thus, detection of time points of the emission start and emission end of X-rays with the short-circuited pixels 62 enables the X-ray imaging assembly 21 to perform sync control for synchronizing operation of the X-ray imaging assembly 21 with the time points of the emission start and emission end of the X-ray generating apparatus 11, without communication of a sync signal with the X-ray generating apparatus 11. Also, it is possible with the short-circuited pixels 62 to perform exposure control to control an exposure amount of an X-ray image appropriately by measuring a total radiation dose of X-rays.

The X-ray imaging assembly 21 is provided with two operating modes, namely, a first operating mode for utilizing the short-circuited pixels 62 in the sync control and a second operating mode for utilizing the short-circuited pixels 62 in the exposure control. The control unit 41 has a function for mode changeover between the two operating modes.

The first operating mode is a mode for use in case of combination with the X-ray generating apparatus 11 having communication compatibility with the communication interface 23a. The second operating mode is a mode for use in case of combination with the X-ray generating apparatus 11 having communication incompatibility with the communication interface 23a.

Figure 4:
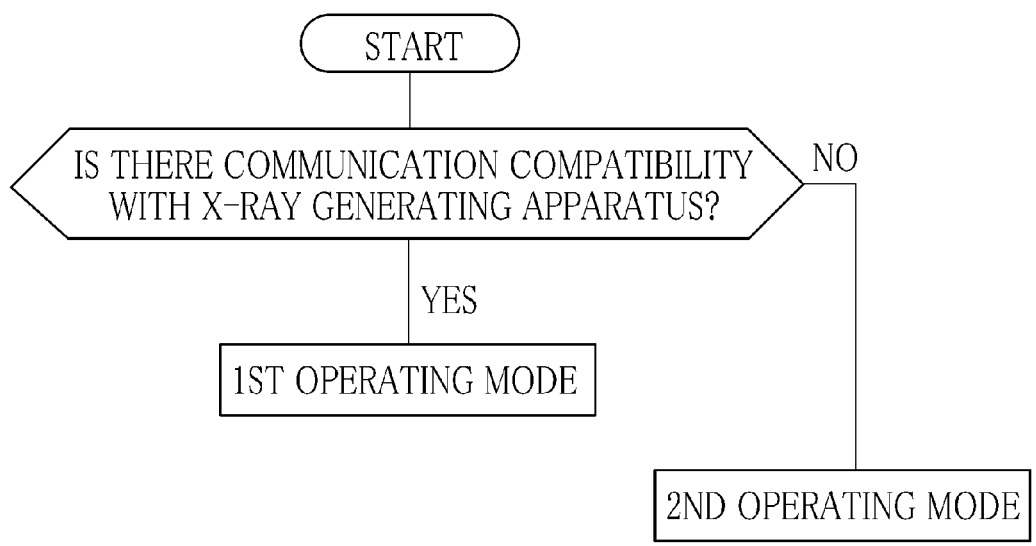
FIG. 4 is an explanatory view illustrating changeover between first and second operating modes in a first embodiment.

As illustrated in the flow chart of FIG. 4, the first operating mode is selected as an operating mode of the X-ray imaging assembly 21 if the X-ray generating apparatus 11 is communicable with the X-ray imaging assembly 21. Also, if the X-ray generating apparatus 11 is not communicable with the X-ray imaging assembly 21, the second operating mode is selected as an operating mode of the X-ray imaging assembly 21. Note that the case where the X-ray generating apparatus 11 is not communicable with the X-ray imaging assembly 21 may be incompatibility of an interface (standard of cable or connector, format of the sync signal, or the like) for the sync control between the X-ray generating apparatus 11 and the X-ray imaging assembly 21, or lack of a communicating function in the X-ray generating apparatus 11, or the like.

Changeover between the first and second operating modes is carried out according to manual operation for the mode selection. Examples of manual mode selection are initializing operation and mode selecting operation. In the initializing operation, a service operator operates the X-ray imaging apparatus 12 at the time of newly installing the X-ray imaging apparatus 12 inclusive of the X-ray imaging assembly 21. In the mode selecting operation, a user inputs with the console unit 24 after installation of the X-ray imaging apparatus 12. Information of the mode selection is stored in an internal memory of the control unit 41. The X-ray imaging assembly 21 operates in the selected mode if there is no change in the mode selection.

If the X-ray generating apparatus 11 for combination with the X-ray imaging assembly 21 is single, no further change of the mode is required subsequently after selecting the mode in the initial setting at the time of installation. If there are a plurality of X-ray generating apparatuses 11 for combination with the X-ray imaging assembly 21, changes in the mode may be required for each of the X-ray generating apparatuses 11 for the combination. It is preferable to operate for the mode selection at the console unit 24.

Instead of or in addition to manual operation of the mode selection, it is possible to detect communication compatibility or incompatibility with the X-ray generating apparatus 11 so that the mode can be changed over automatically according to a result of the detection. For example, the communication compatibility or incompatibility with the X-ray generating apparatus 11 is detected by the control unit 41 or the imaging control unit 23b. To this end, the communication interface 23a or 33 sends a test signal to the X-ray generating apparatus 11 and determines existence or non-existence of a response from the same.

The X-ray imaging assembly 21 causes the indicator 28 to display the operating mode selected by the manipulation of mode selection or automatic changeover of the mode. Thus, a user can check the selected operating mode according to appearance of the X-ray imaging assembly 21.

Figure 5:
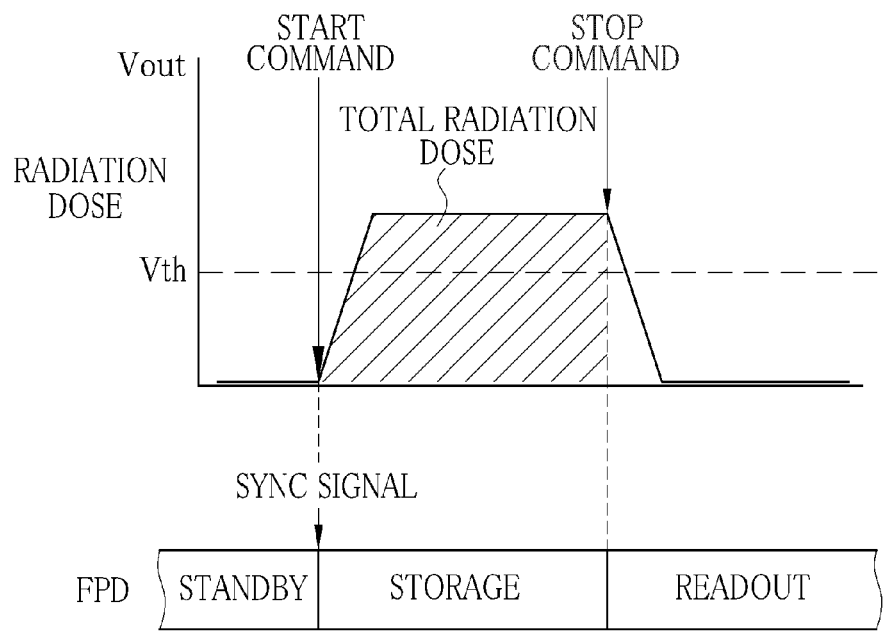
FIG. 5 is an explanatory view illustrating steps of the first operating mode in the first embodiment.

FIG. 5 illustrates a total radiation dose of X-rays and an operation state of the flat panel detector 36 in the case of operating the X-ray imaging assembly 21 in the first operating mode, the flat panel detector 36 being controlled according to the total radiation dose. The radiation dose of X-rays is in a shape of substantially a trapezoid in a graph of which time is taken on a horizontal axis and the radiation dose (output voltage Vout) of X-rays is taken on a vertical axis. When the X-ray source 13 starts emitting X-rays upon receiving a start command, a radiation dose of X-rays gradually increases, and comes up to a peak value according to a tube current set in the imaging condition, and keeps a constant state in the vicinity of the peak value until receiving a stop command. When the emission of X-rays is stopped upon receiving the stop command in the X-ray source 13, the radiation dose of X-rays gradually decreases, and then becomes "0" to stop the emission of X-rays completely.

In the first operating mode, the control unit 41 sets a threshold of a total radiation dose of X-rays according to a request of examination input through the console unit 24, namely, sex, age, body part, purpose for imaging, and the like of a patient. When an instruction for standby for imaging is input by the controller 23, the control unit 41 sets the flat panel detector 36 in a standby state. In the standby state, the control unit 41 causes the flat panel detector 36 to carry out the resetting. As the first operating mode is a mode selected in the case of communication compatibility with the X-ray generating apparatus 11, a control of start synchronization of the X-ray imaging assembly 21 is performed in a well-known signal communication method. Specifically, the control unit 41 receives an emission start signal via the controller 23 upon being output by the radiation source control assembly 14. The control unit 41, upon receiving the emission start signal, turns off the TFTs 43 of the pixels 37 and changes over the same from the standby state to the storage step. As the TFTs 43 are turned off, the pixels 37 are caused to store the signal charge according to the dose of the applied X-rays.

When the storage step is started in the first operating mode, a total radiation dose of X-rays starts being measured. Even when the TFTs 43 of the pixels 37 are turned off, the short-circuited pixels 62 are always short-circuited with the signal lines 48. The control unit 41 can measure the total radiation dose of X-rays according to an output of the short-circuited pixels 62 flowing to the signal lines 48 while X-rays are emitted. The control unit 41 accumulates the output voltage Vout of the short-circuited pixels 62, measures the total radiation dose of X-rays, and compares a result of the measurement with a threshold. When the total radiation dose of X-rays reaches the threshold, the control unit 41 causes the controller 23 to send a stop signal to the radiation source control assembly 14. The radiation source control assembly 14 upon receiving the stop signal sends the stop command to the X-ray source 13 to stop emission of X-rays. Also, the control unit 41 terminates the storage step of the flat panel detector 36 at the same time as sending of the stop signal, for changeover to the readout step.

In the first operating mode described above, real-time processing is required for communication to control the total radiation dose of X-rays at high precision, in relation to a sync signal for time points of an emission start and emission end of an emission start signal and stop signal in communication between the X-ray imaging assembly 21 and the radiation source control assembly 14 for the sync control. Therefore, it is necessary to carry out communication rapidly between the communication interface 33, the communication interface 23a and the communication device 14c in the X-ray imaging assembly 21, the controller 23 and the radiation source control assembly 14. The communication interface 33, the communication interface 23a and the communication device 14c are provided with two communication modes, namely a high speed communication mode for use in communication of a sync signal with which rapidity is important, and a normal mode for use in communication with which rapidity is not very important. The normal mode is used for sending and receiving a command for instructing performance of a particular task at the time of setting the apparatuses and operation control. The command is a signal including binary information (0001, 1001 and the like) expressing meanings of various instructions. A task of decoding is required for the received command for recognizing a meaning of the command. As the normal mode is a communication mode inclusive of the decoding, surplus time is required for decoding in the process time.

The high speed communication mode is a mode in which decoding can be omitted. Specifically, a sender sends a sync signal such as an emission start signal and stop signal only with a pulse wave in the high speed communication mode. A recipient receives the pulse wave, detects edges of a rise and fall of the pulse wave and judges that the sync signal is received. For example, the emission start signal is a signal sent by the X-ray generating apparatus 11 to the X-ray imaging apparatus 12, and is transmitted sequentially from the communication device 14c of the X-ray generating apparatus 11 to the communication interface 23a of the controller 23 and to the communication interface 33 of the X-ray imaging assembly 21. The communication device 14c sends a pulse wave to the communication interface 23a as an emission start signal. The communication interface 23a determines the emission start signal at the time of detecting the rise of the pulse wave, and transfers the received pulse wave to the communication interface 33. Also, the communication interface 33 determines the emission start signal at the time of detecting the rise of the pulse wave, and notifies the control unit 41 thereof.

According to this, it is possible to omit the processing of decoding in the normal mode. Rapid real-time communication is possible. Note that an edge of the pulse wave is detected in the high speed communication mode. However, it is possible to transmit a command of an emission start signal expressed as binary information instead of the pulse wave, and to detect an edge included in the command. Also, it is possible in the high speed communication mode to utilize a signal of light or sound besides the electric signal for communication. Furthermore, although the high speed communication mode is provided in each of the communication interface 33, the communication interface 23a and the communication device 14c for command communication, it is possible to install a communication device in addition to the communication interface 33, the communication interface 23a and the communication device 14c for high speed communication specialized for the sync signal.

Figure 6:
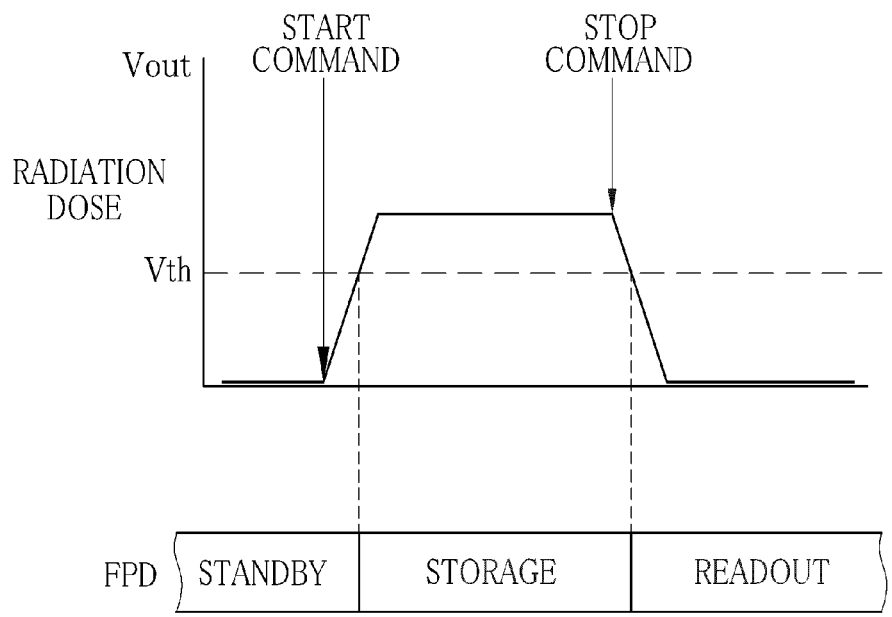
FIG. 6 is an explanatory view illustrating steps of the second operating mode in the first embodiment.

As illustrated in FIG. 6, the second operating mode is a mode selected in case of non-communicability with the X-ray generating apparatus 11. The controller 23 and the X-ray imaging assembly 21 cannot receive an emission start signal from the X-ray generating apparatus 11. Thus, the control unit 41 performs the control of start synchronization and the control of stop synchronization according to an auto-detecting method.

In the control of start synchronization, the control unit 41 in the standby state measures a radiation dose of X-rays according to an output voltage Vout corresponding to a signal charge generated by the short-circuited pixels 62, and starts monitoring changes in the radiation dose of X-rays. The control unit 41 compares the output voltage Vout with a predetermined threshold Vth, and if the output voltage Vout becomes higher than the threshold Vth, detects an emission start of X-rays.

When the emission start of X-rays is detected, the control unit 41 turns off the TFTs 43 of the pixels 37 and changes over from the standby state to the storage step in a manner similar to the first operating mode. After the changeover to the storage step, the control unit 41 starts the control of stop synchronization. Even when the TFTs 43 of the pixels 37 are turned off, the short-circuited pixels 62 are always short-circuited with the signal lines 48. While X-rays are emitted, the control unit 41 continues monitoring changes in a radiation dose of X-rays according to an output of the short-circuited pixels 62 flowing to the signal lines 48. When a stop command is input to the X-ray source 13 upon a lapse of the irradiation time set in the imaging condition, intensity of X-rays starts decreasing. When the output voltage Vout becomes equal to or less than the threshold Vth, the control unit 41 detects a start of the decrease in the X-ray intensity, and detects an emission end of X-rays. In response, the control unit 41 terminates the storage step of the flat panel detector 36 and changes over to the readout step.

Figure 7:
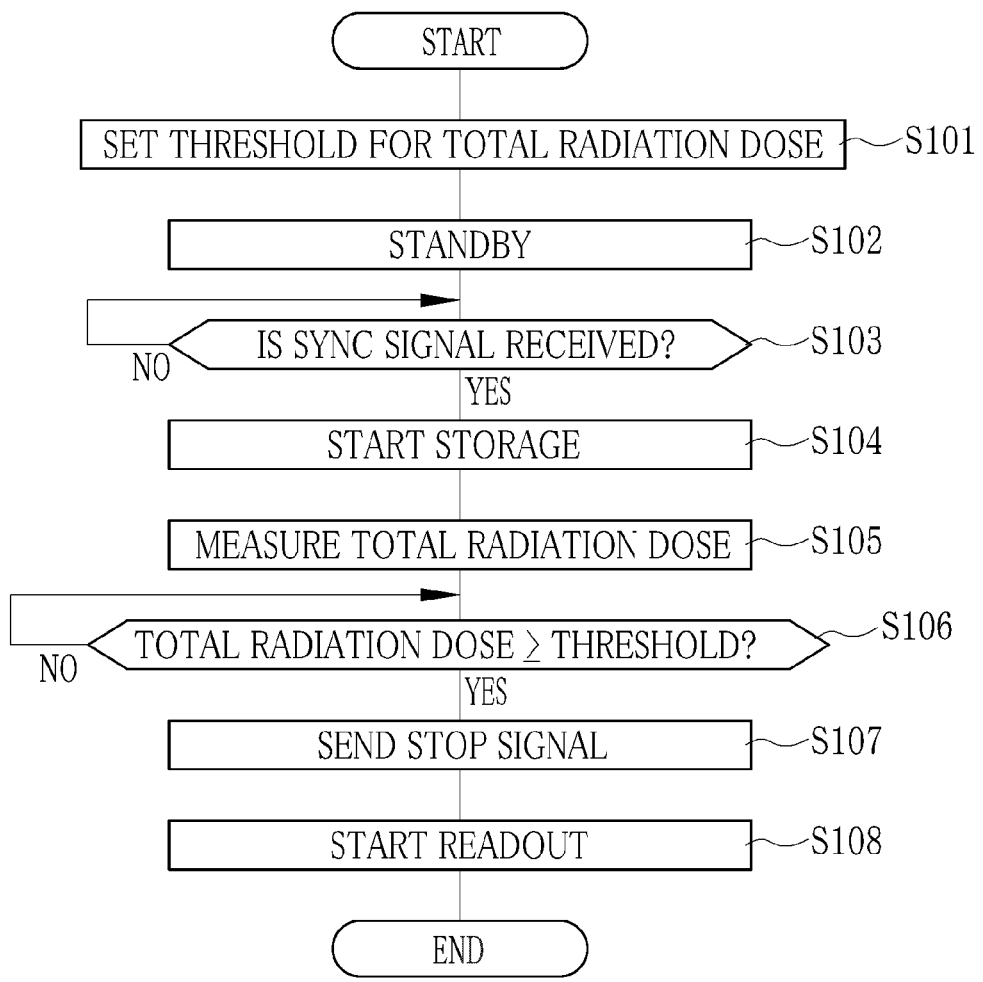
FIG. 7 is a flow chart illustrating a control of the FPD in the first operating mode in the first embodiment.

The operation of carrying out of the first operating mode in the X-ray imaging assembly 21 incorporated in the X-ray imaging system 10 of FIG. 1 is described by referring to a flow chart of FIG. 7. A body part of the object H and the irradiation position of the X-ray source 13 are set relative to the imaging stand 22 where the X-ray imaging assembly 21 is set. An imaging condition is set in the X-ray source 13, inclusive of a tube voltage, tube current, irradiation time and the like. The console unit 24 inputs a request of examination to the controller 23, namely, sex, age, body part, purpose for imaging, and the like of a patient. The control unit 41 of the X-ray imaging assembly 21 sets a threshold for the total radiation dose of X-rays according to the request of examination (S101).

When the control unit 41 of the X-ray imaging assembly 21 is supplied by the controller 23 with an input of instruction of standby for imaging, the flat panel detector 36 (FPD as image detector) changes over to the standby state (S102). When a start command for emission is input to the X-ray source 13 by depression of the radiation switch 15, the X-ray source 13 starts emission of X-rays to the object H. At the same time, the radiation source control assembly 14 sends an emission start signal to the controller 23. The control unit 41, upon receiving the emission start signal through the controller 23 (S103), starts the flat panel detector 36 to operate for the storage step (S104).

During the storage step of the flat panel detector 36, the control unit 41 accumulates the output voltage Vout, measures the total radiation dose of X-rays (S105), and compares the total radiation dose of X-rays with the threshold (S106). When the total radiation dose of X-rays comes up to the threshold, the control unit 41 sends a stop signal to the radiation source control assembly 14 through the controller 23 (S107). The radiation source control assembly 14 upon receiving the stop signal sends a stop command to the X-ray source 13 to stop emission of X-rays. At the same time as sending of the stop signal, the control unit 41 stops the flat panel detector 36 from the storage step, and sets the flat panel detector 36 for the readout step (S108). An X-ray image being read is written to the memory 56 and transmitted to the console unit 24.

Figure 8:
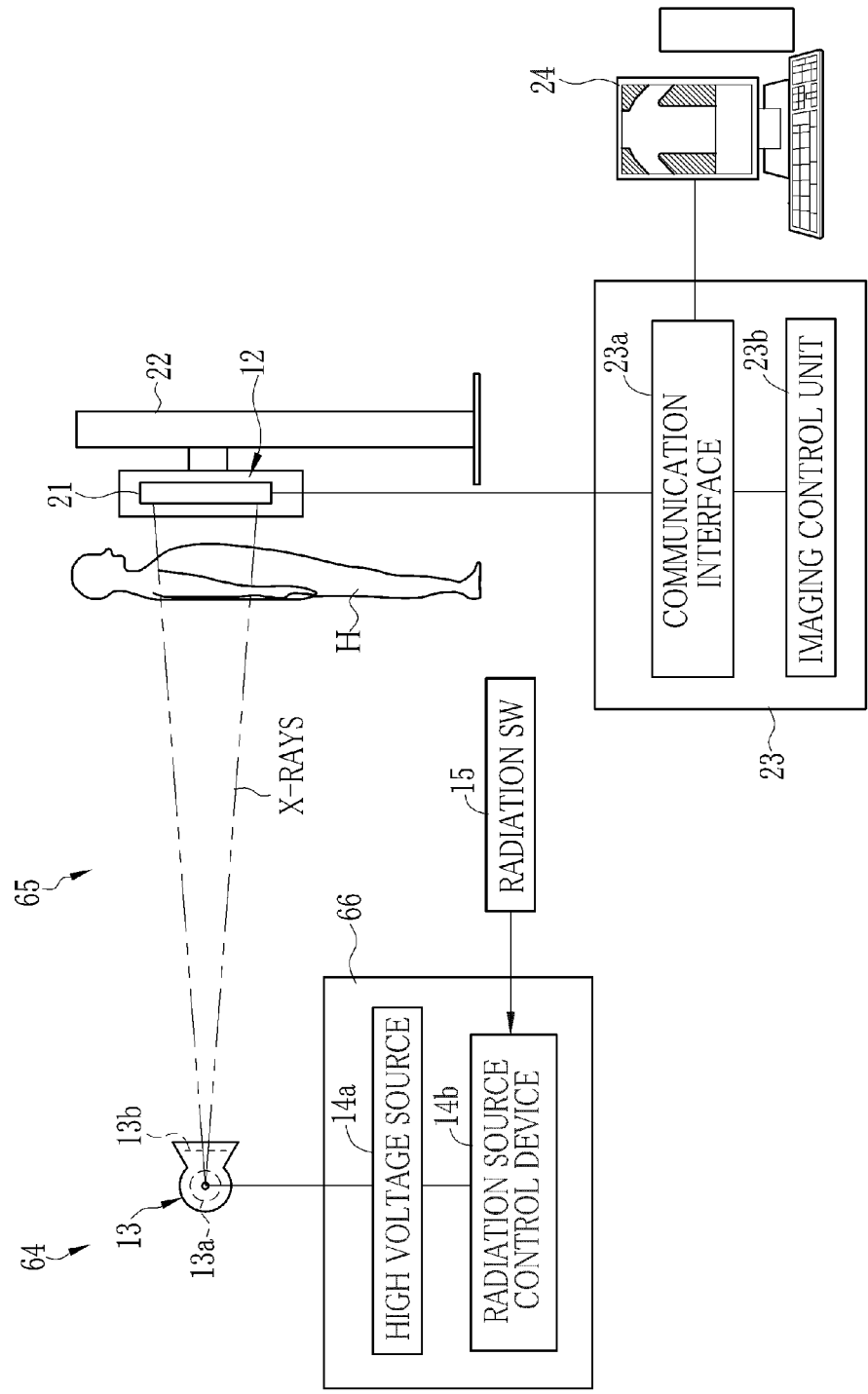
FIG. 8 is an explanatory view schematically illustrating an X-ray imaging system having an X-ray generating apparatus incompatible with the X-ray imaging apparatus for communication compatibility.
Figure 9:
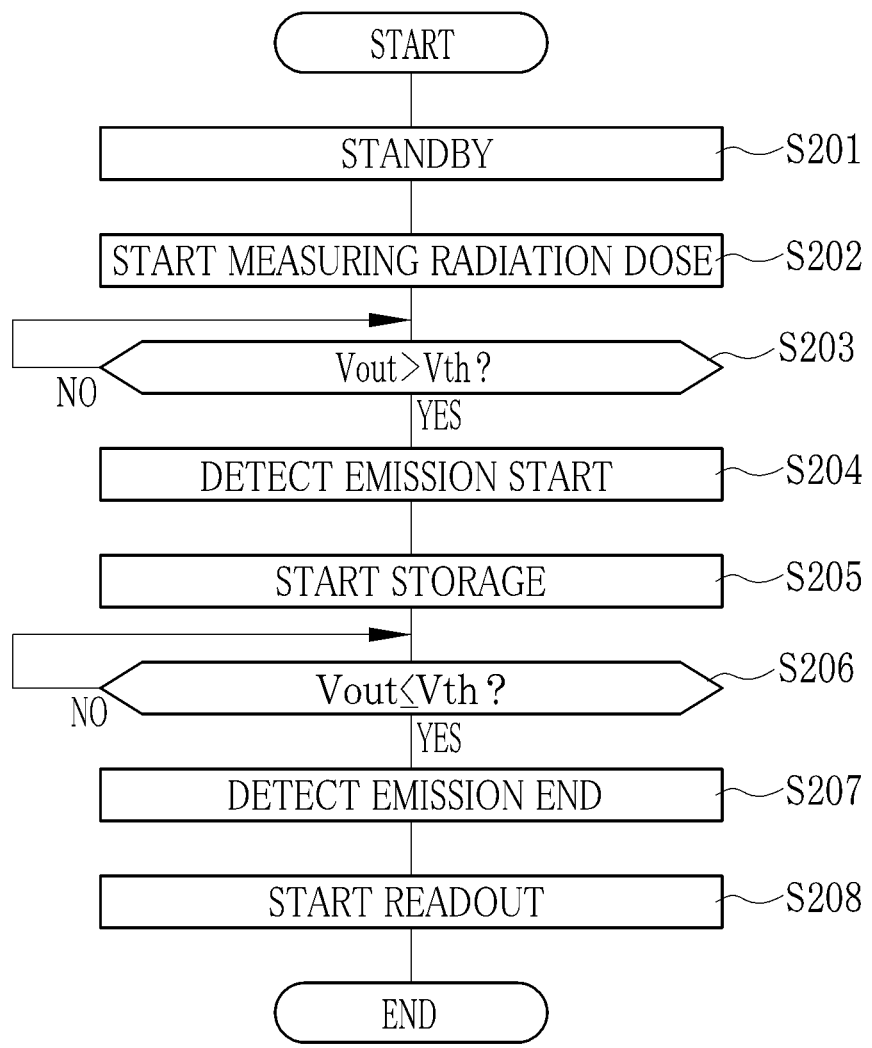
FIG. 9 is a flow chart illustrating a control of the FPD in the second operating mode in the first embodiment.

The operation according to the second operating mode is described with reference to a flow chart of FIG. 9, the second operating mode being selected when the X-ray imaging assembly 21 is combined with an X-ray imaging system 65 having an X-ray generating apparatus 64 without a communicating function as illustrated in FIG. 8. Note that the X-ray imaging system 65 is structurally the same as the X-ray imaging system 10 of FIG. 1 except for a difference in that a radiation source control unit 66 does not have the communication device 14c and is incompatible with the controller 23 for the communication compatibility. Elements in the X-ray imaging system 65 similar to those in FIG. 1 are designated with identical reference numerals. Also, the second operating mode is selected also in the case of communication incompatibility between the communication device 14c of the X-ray generating apparatus 11 of FIG. 1 and an interface of the X-ray imaging apparatus 12. The operation of this construction is similar to that of FIG. 8.

In a manner similar to the first operating mode, the positioning of the irradiation position, setting of an imaging condition, inputting of a request of the examination, and the like are carried out in the second operating mode. When a command for standby of imaging is input to the control unit 41 of the X-ray imaging assembly 21 by the controller 23, the flat panel detector 36 is changed over to the standby state (S201). Upon changeover to the standby state, the flat panel detector 36 starts resetting, and starts measurement of a radiation dose of X-rays (S202).

When an emission start command is input to the X-ray source 13 by depressing the radiation switch 15, the X-ray source 13 starts applying X-rays to the object H. The flat panel detector 36 compares the output voltage Vout with the threshold Vth, and monitors a change of a radiation dose of X-rays (S203). When the radiation dose of X-rays increases to make the output voltage Vout higher than the threshold Vth, then an emission start of X-rays is detected (S204). As the emission start is detected, the flat panel detector 36 turns off the TFTs 43 of the pixels 37 to start the storage step (S205).

Even during the storage step, the flat panel detector 36 compares the output voltage Vout with the threshold Vth to monitor a change in the radiation dose of X-rays (S206). When the irradiation time set in the imaging condition has elapsed, the X-ray source 13 receives an input of a stop command, so that intensity of X-rays starts decreasing. When the output voltage Vout becomes equal to or lower than the threshold Vth, the flat panel detector 36 detects a start of the decrease of the intensity of X-rays, to determine an emission end (S207). The control unit 41 terminates the storage step of the flat panel detector 36 upon determining the emission end, and starts the readout step (S208). An X-ray image being read is written to the memory 56 and transmitted to the console unit 24.

As described heretofore, it is possible in the present embodiment to select one of using methods of the short-circuited pixels 62 suitably according to communication compatibility or incompatibility with the X-ray generating apparatus in the X-ray imaging system having the X-ray imaging assembly 21. In case of the communication compatibility with the X-ray generating apparatus, an auto-detecting method is not required in sync control. The short-circuited pixels 62 can be used for exposure control. Consequently, overexposure of an X-ray image or overexposure to an object can be prevented. In case of the communication incompatibility with the X-ray generating apparatus, the short-circuited pixels 62 are used for sync control in the auto-detecting method. An X-ray imaging system can be constructed by combining an X-ray generating apparatus known with an X-ray film or IP plate, an X-ray generating apparatus with incompatibility of a communication interface, for example, due to a difference in the manufacturer, with the X-ray imaging assembly 21.

[Second Embodiment]

Figure 10:
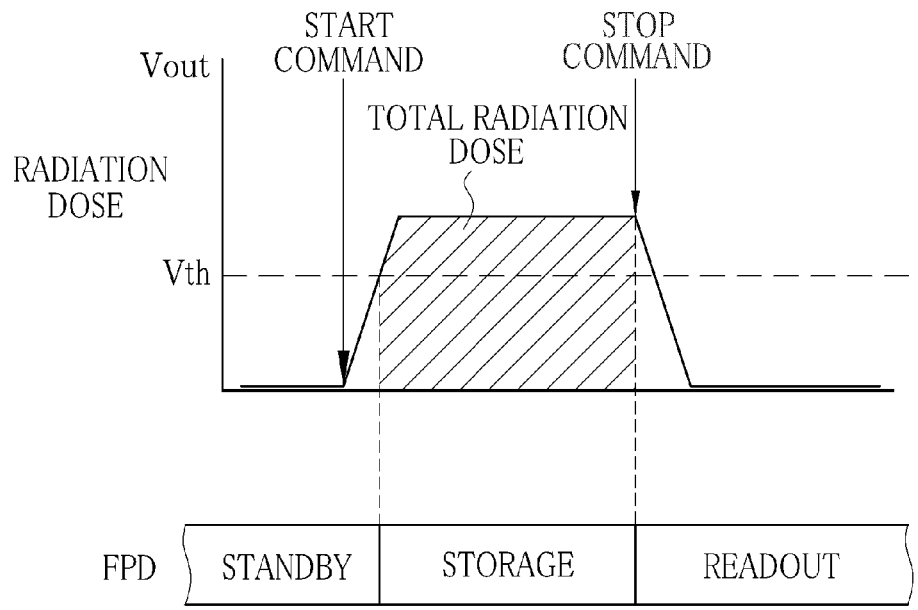
FIG. 10 is an explanatory view illustrating steps of the first operating mode in a second embodiment.

In the first operating mode of the first embodiment, a sync control of a signal communication method for starting the storage step of the flat panel detector 36 is performed in synchronism with an emission start signal transmitted by the radiation source control assembly 14. As illustrated in FIG. 10, an emission start of X-rays from the X-ray source 13 can be detected by the short-circuited pixels 62 in the first operating mode, so that the storage step of the flat panel detector 36 can be started in synchronism therewith. For this situation, the short-circuited pixels 62 are utilized for both of the control of start synchronization and exposure control.

Figure 11:
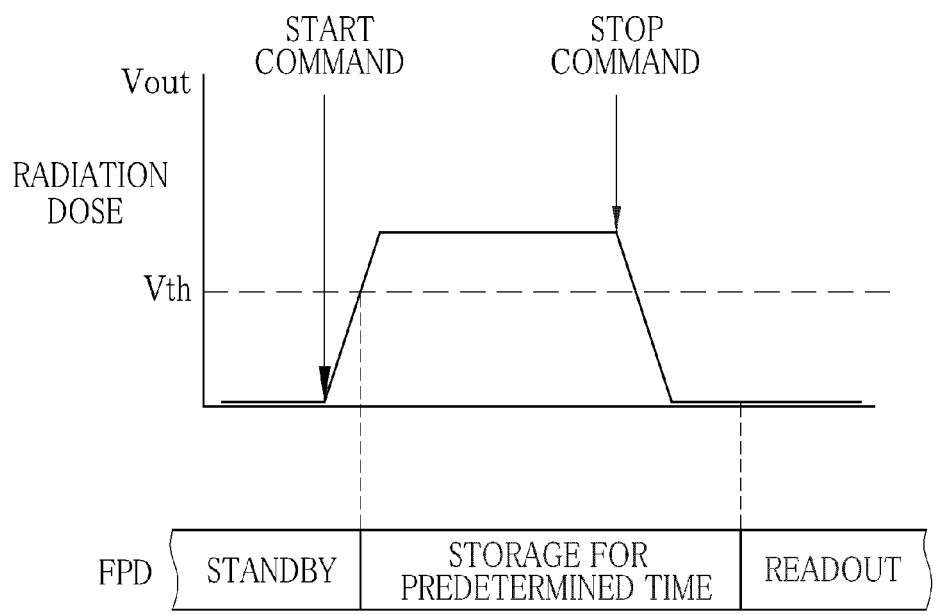
FIG. 11 is an explanatory view illustrating steps of the second operating mode in the second embodiment.

In the second operating mode of the first embodiment, the storage step of the flat panel detector 36 is terminated by detecting an emission end of X-rays with the short-circuited pixels 62. However, it is possible as illustrated in FIG. 11 to terminate the storage step upon lapse of a predetermined time from the start of the storage step. In this manner, it is possible in the second operating mode to perform at least the control of start synchronization. It is unnecessary to perform the control of stop synchronization of the auto-detecting method of detecting the time point of the emission end of X-rays. Also, the flat panel detector may be previously set in the storage step by manual operation and receive application of X-rays for imaging. For this structure, it is possible to detect only the emission end without detecting the emission start, and change over from the storage step to the readout step. In the second operating mode, the total radiation dose of X-rays can be measured so that the storage step of the flat panel detector 36 can be terminated upon reach of the total radiation dose to the threshold. As the transmission of a stop signal to the X-ray generating apparatus 11 is impossible, the irradiation of the X-ray generating apparatus 11 cannot be stopped. A period of the storage step in the X-ray imaging assembly 21 can only be adjusted.

Figure 12:
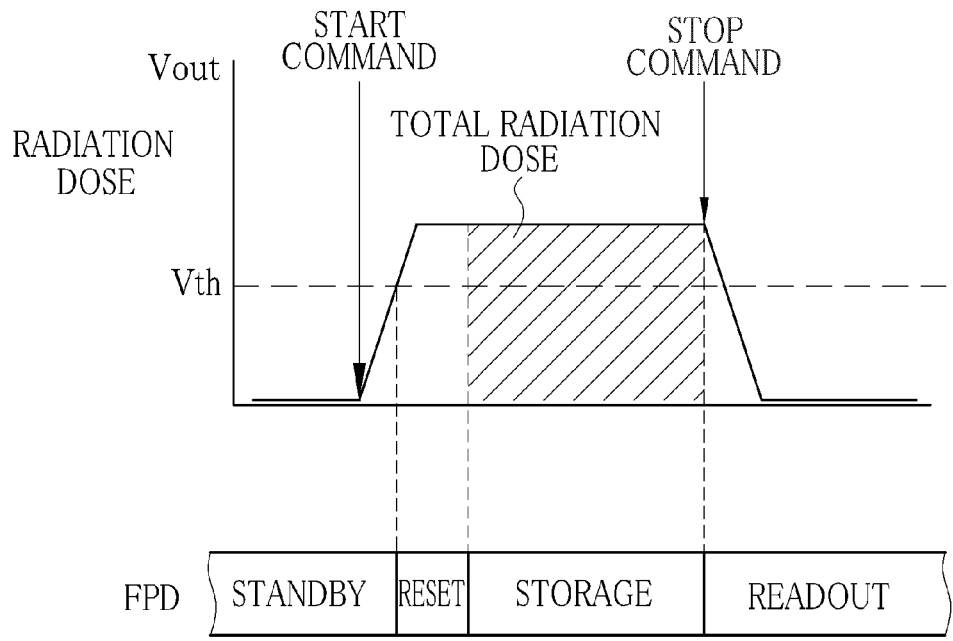
FIG. 12 is an explanatory view illustrating a variant of the first operating mode in the second embodiment.
Figure 13:
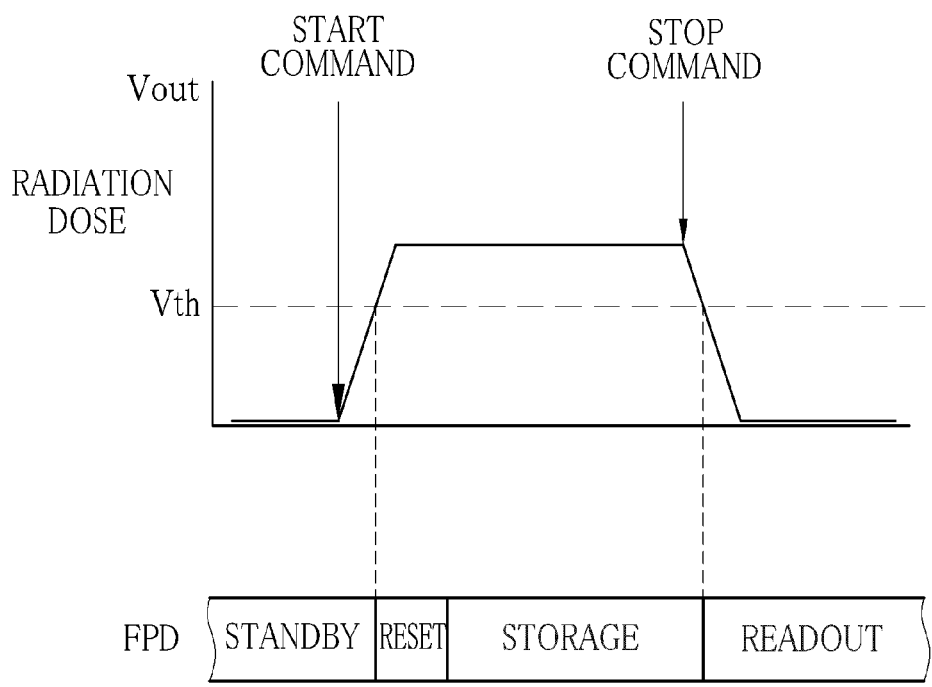
FIG. 13 is an explanatory view illustrating a variant of the second operating mode in the second embodiment.

In the first embodiment, the pixels 37 are reset while the flat panel detector 36 is in the standby. However, it is possible to carry out the resetting after detecting an emission start of X-rays and then change over to the storage step, as illustrated in FIG. 12 for the exposure control and in FIG. 13 for the sync control. An example of the resetting carried out at this time point may be the sequential resetting or simultaneous resetting or total pixel resetting. However, it is preferable to carry out the total pixel resetting so that the resetting can be as short as possible.

[Third Embodiment]

Figure 14:
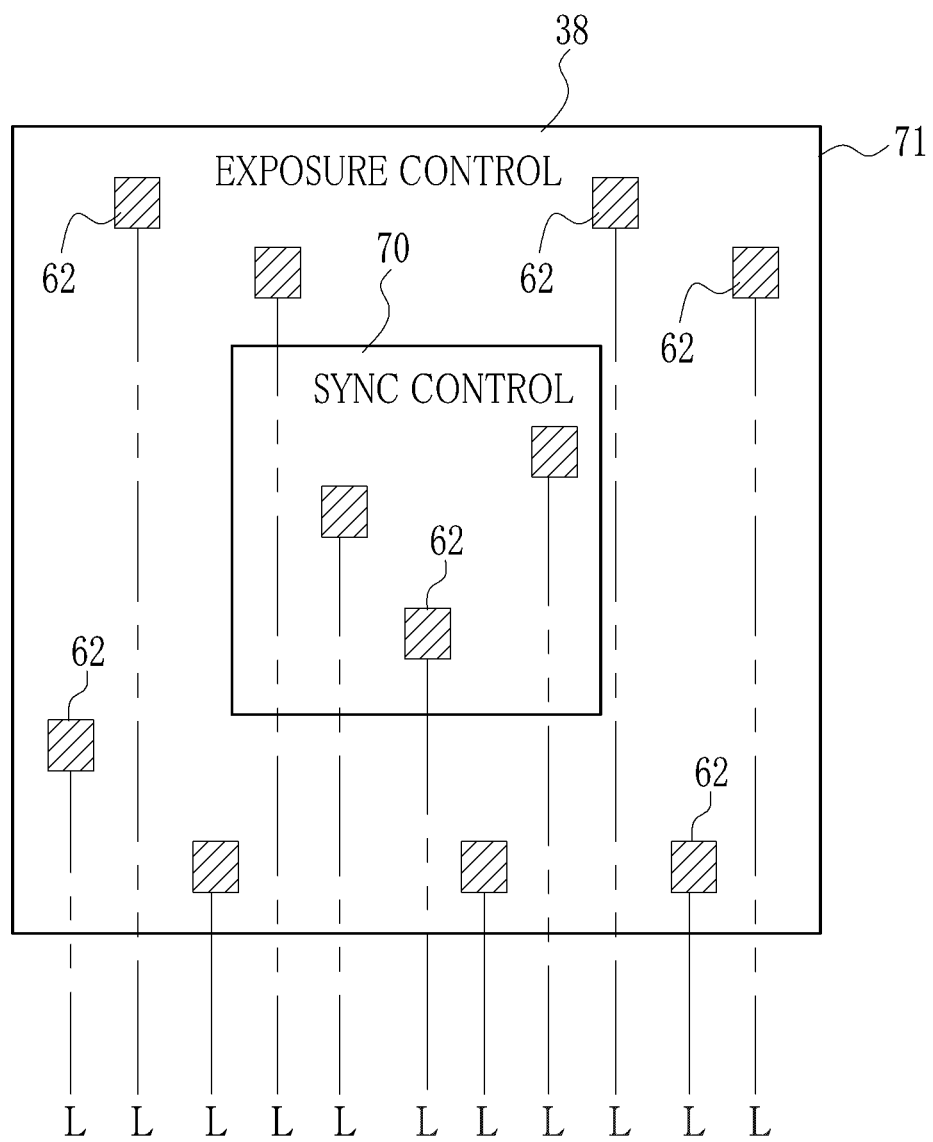
FIG. 14 is an explanatory view illustrating an imaging area of the FPD of third and fourth embodiments.

As illustrated in FIG. 14, the imaging area 38 of the flat panel detector 36 can be split into two partial areas 70 and 71 including a central partial area 70 and a side partial area 71, the central partial area 70 being disposed at a center, the side partial area 71 being disposed around the central partial area 70. The short-circuited pixels 62 are disposed in the central and side partial areas 70 and 71, which can be utilized discretely between the exposure control and sync control.

For example, a radiation dose of X-rays applied to the flat panel detector 36 by the X-ray source 13 is higher in the central partial area than in the side partial area. Thus, the central partial area 70 is used for sync control. The side partial area 71 is used for exposure control. Specifically, the control unit 41 performs the sync control according to an output of the short-circuited pixels 62 disposed in the central partial area 70, and performs the exposure control according to an output of the short-circuited pixels 62 disposed in the side partial area 71. As the short-circuited pixels 62 are connected with respectively the signal lines L, the control unit 41 selects the central and side partial areas 70 and 71 by selecting the signal lines L. At the time of the sync control, the central partial area 70 with the higher radiation dose of X-rays is used to detect an emission start and emission end of X-rays with good precision. At the time of the exposure control, the side partial area 71 is used to prevent an error in the exposure due to under-exposure, because the total radiation dose is measured with X-rays of a lower radiation dose than the central area.

In view of events of actual imaging, an object smaller than the area size of the imaging area 38, such as a hand or foot, is likely to be disposed at the center of the imaging area 38. The side area is likely to be a through area to which X-rays are applied directly without an object. For this situation, X-rays incident upon the imaging area 38 are more in the side area than at the center. In reverse to the embodiment of FIG. 14, it is preferable to use the side partial area 71 for the sync control and to use the central partial area 70 for the exposure control.

Fourth Embodiment

Also, sensitivity of pixels in a partial area for use in the exposure control or sync control can be made relatively higher than sensitivity in the remaining partial area not for use in the control. For example, sync control is performed in a flat panel detector having the central and side partial areas 70 and 71 illustrated in FIG. 14. The sensitivity of the short-circuited pixels 62 of the central partial area 70 for use in the sync control is set higher than that of the short-circuited pixels 62 in the side partial area 71. At the time of the exposure control, the sensitivity of the short-circuited pixels 62 of the side partial area 71 for use in the exposure control is set higher than that of the short-circuited pixels 62 in the central partial area 70. Accordingly, it is possible to perform both of the exposure control and sync control at high precision even for imaging with a low radiation dose of X-rays. For example, a gain of an amplifier for connection with the signal line L can be raised in order to change the sensitivity. Also, it is possible to carry out binning to add up outputs of a plurality of the short-circuited pixels 62 for raising the sensitivity.

Note that partial areas are not limited to the two partial areas or the central and side partial areas 70 and 71 to which the imaging area is split as described above. The imaging area can be split into three or more partial areas. A shape and area size of the partial areas can be equal or can be different between those.

Furthermore, each one of the third and fourth embodiments can be combined with the first embodiment. The X-ray imaging assembly 21, if the X-ray generating apparatus 11 has communication compatibility, is set in the first operating mode, in which the sync control is performed in the signal communication method. The short-circuited pixels 62 in the central and side partial areas 70 and 71 are used for the sync control in the second operating mode and for the exposure control.

[Fifth Embodiment]

Although the above embodiments are described with imaging of a still image, motion imaging can be carried out in the X-ray imaging assembly 21, such as radiographic imaging. As illustrated in FIG. 15, a plurality of X-ray pulses are applied successively for imaging as X-rays in a pulsed form in the motion imaging. In this event, the control unit 41 detects a rise and fall of each of the X-ray pulses with the short-circuited pixels 62 to detect time points of emission of the X-ray pulses. The flat panel detector 36 can be changed over between the standby, storage step and readout step in synchronism with the detected time points.

Also, it is possible in the control unit 41 to measure a radiation dose with one X-ray pulse from the short-circuited pixels 62 in the storage step, and control an output gain of the amplifier in the readout step according to a result of the measurement. The gain control can be performed by, for example, the integrating amplifiers 49, or by amplifiers (not shown) connected with output terminals of the integrating amplifiers 49 to amplify the voltage signals D1-Dm. As the short-circuited pixels 62 are disposed in the imaging area 38 discretely from one another, it is possible to estimate the contrast of X-ray image according to outputs of the short-circuited pixels 62 of different positions, to control the output gain according to the estimated contrast.

In the above embodiments, the short-circuited pixels disposed in the imaging area measure a radiation dose of X-rays. It is possible to measure the radiation dose of X-rays accurately because the short-circuited pixels are structurally the same as regular pixels and have an equal sensitivity to X-rays. It is possible with high precision to detect an emission start, emission end, and total radiation dose. Owing to substantially the same structure, the short-circuited pixels can be manufactured easily, with a small increase in the manufacturing cost.

There are various forms of radiation detectors besides the short-circuited pixels. For example, a bias voltage is applied to a photo diode constituting a pixel. A bias current flowing in the bias line is changed according to an amount of the signal charge generated in the photo diode. A radiation dose of X-rays can be measured by detecting the bias current. Even when the TFT of pixels is turned off, a leak current of a low level flows in a signal line according to an amount of the signal charge generated in the photo diode. A radiation dose of X-rays can be measured by detecting the leak current. In the methods of detecting the bias current or leak current, a detector for detecting currents is the radiation detector. Also, a radiation detector can be incorporated in an X-ray imaging apparatus, inclusive of elements specialized for detecting X-rays in a different form from the short-circuited pixels. The elements can be disposed inside or outside the imaging area. Also, an ionization chamber or other known radiation detectors may be provided.

Also, although the flat panel detector of the TFT type in which the TFT matrix substrate is formed by use of the glass substrate, a flat panel detector may be constituted by use of a CMOS image sensor or CCD image sensor in which a semiconductor substrate is used. When the CMOS image sensor is used, the following merits are obtained. It is possible by use of the CMOS image sensor to carry out so-called non-destructive readout in which a signal charge stored in pixels is read as a voltage signal through amplifiers in connection with the pixels without flowing out of the signal charge for the pixels to the signal lines for the readout step. So it is possible even during the storage step to measure the strength of X-rays by selecting any of the pixels in an imaging area and by reading the signal charge from the pixel. Consequently, it is possible in use of the CMOS image sensor to use any of the normal pixels as a radiation detector for measurement of the radiation dose without a special radiation detector for the measurement of the radiation dose of X-rays in the manner of the short-circuited pixels described above.

Furthermore, an X-ray imaging apparatus of the present invention can have any one of various forms other than the above embodiments.

The X-ray imaging apparatus is used for the X-ray imaging system installed in an imaging room in a hospital, and also can be carried in a medical cart which is used for moving between hospital rooms and one room after another for the purpose of imaging, and also can be adapted to a portable system which can be used for X-ray imaging in a site requiring emergency medicine due to an accident, disaster or the like or in a home of a patient receiving a health care service at home.

In the above examples, the controller 23 for imaging is separate from the X-ray imaging assembly. However, the controller 23 can be a portion of a single machine including the X-ray imaging assembly. For example, a function of the imaging controller can be incorporated in a control unit of the X-ray imaging assembly.

In the above embodiments, the portable type of X-ray imaging assembly has been described as examples. However, the present invention is applicable to an installed type of X-ray imaging assembly.

The present invention is also applicable to an imaging system for use with gamma rays or other rays without limitation to X-rays.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiographic imaging apparatus for use with a radiation generating apparatus for emitting radiation, comprising:
    an image detector, having an imaging area in which plural pixels are arranged in arrays for storing a signal charge according to a radiation dose of said radiation upon receiving said radiation from said radiation generating apparatus, for detecting a radiation image by receiving radiation transmitted through an object;
    a radiation detector for outputting a detection signal according to said radiation dose, in order to detect an emission start of said radiation from said radiation generating apparatus, and/or in order to measure a total radiation dose of said radiation;
    a communication interface for communicating with said radiation generating apparatus;
    a mode selector for selectively setting one of first and second operating modes;
    wherein said first operating mode is used in case of combination with said radiation generating apparatus with which said communication interface has communication compatibility, for performing at least an exposure control for measuring said total radiation dose according to said detection signal from said radiation detector;
    said second operating mode is used in case of combination with said radiation generating apparatus with which said communication interface has communication incompatibility, for performing at least a control of start synchronization for detecting said emission start according to said detection signal from said radiation detector and starting a storage step of storing said signal charge of said image detector in synchronism with said emission start;
    a controller for controlling said image detector according to said one operating mode selectively set by said mode selector.

2. A radiographic imaging apparatus as defined in claim 1, wherein in said first operating mode, said controller starts said storage step in synchronism with an emission start signal transmitted to said communication interface by said radiation generating apparatus.

3. A radiographic imaging apparatus as defined in claim 2, wherein in said first operating mode, said controller measures said total radiation dose by accumulating said detection signal from said radiation detector, and when said total radiation dose reaches a threshold, causes said communication interface to transmit a stop signal to said radiation generating apparatus to stop emission of said radiation.

4. A radiographic imaging apparatus as defined in claim 3, wherein when said total radiation dose reaches said threshold, said controller terminates said storage step of said image detector.

5. A radiographic imaging apparatus as defined in claim 1, wherein in said second operating mode, said controller detects an emission end of said radiation from said radiation generating apparatus according to said detection signal from said radiation detector in addition to said control of said start synchronization, and terminates said storage step of said image detector in synchronism with said emission end.

6. A radiographic imaging apparatus as defined in claim 1, wherein in said second operating mode, said controller terminates said storage step upon a lapse of a predetermined time after a start of said storage step.

7. A radiographic imaging apparatus as defined in claim 2, wherein in said first and second operating modes, said controller carries out resetting in which a signal charge of said pixels is reset after detecting said emission start and before starting said storage step.

8. A radiographic imaging apparatus as defined in claim 1, wherein in said first operating mode, said controller performs said control of said start synchronization in addition to said exposure control.

9. A radiographic imaging apparatus as defined in claim 1, wherein said mode selector selects said operating modes according to manual operation for mode selection.

10. A radiographic imaging apparatus as defined in claim 1, wherein said mode selector detects communication compatibility or incompatibility with said radiation generating apparatus, and automatically selects said operating modes according to a result of detection.

11. A radiographic imaging apparatus as defined in claim 1, further comprising a notifier for notifying information as to which of said first and second operating modes is selected.

12. A radiographic imaging apparatus as defined in claim 2, wherein in said first operating mode, said emission start signal from said radiation generating apparatus is constituted by a pulse wave, and said communication interface notifies said controller of receiving said emission start signal upon detecting an edge of said pulse wave.

13. A radiographic imaging apparatus as defined in claim 1, wherein said radiation detector is disposed in said imaging area.

14. A radiographic imaging apparatus as defined in claim 13, wherein said radiation detector is disposed in each one of plural partial areas defined by splitting said imaging area;
said controller changes over said partial areas for use between said exposure control and said control of said start synchronization.

15. A radiographic imaging apparatus as defined in claim 14, wherein said plural partial areas include a central partial area disposed at a center of said imaging area and a side partial area disposed in a periphery of said central partial area;
said controller uses said central and side partial areas selectively in said exposure control and said control of said start synchronization.

16. A radiographic imaging apparatus as defined in claim 15, wherein said controller changes a sensitivity of said radiation detector in said partial areas for use in respectively said exposure control and said control of said start synchronization.

17. A radiographic imaging apparatus as defined in claim 13, wherein said radiation detector is a short-circuited pixel where one of said pixels is always short-circuited with a signal line for reading out said signal charge from said pixel, for outputting said signal charge to said signal line according to said radiation dose.

18. A radiographic imaging apparatus as defined in claim 1, wherein said image detector operates for motion imaging by receiving plural radiation pulses of said radiation emitted successively by said radiation generating apparatus;
in said motion imaging, said controller detects an edge of said radiation pulses according to said detection signal from said radiation detector, and synchronizes said storage step of said image detector with emission of said radiation pulses.

19. A radiographic imaging apparatus as defined in claim 18, wherein said controller measures said radiation dose per said radiation pulses according to said detection signal from said radiation detector, and controls an output gain of said signal charge according to a result of measurement.

20. A control method for a radiographic imaging apparatus for use with a radiation generating apparatus for emitting radiation, said radiographic imaging apparatus including an image detector, having an imaging area in which plural pixels are arranged in arrays for storing a signal charge according to a radiation dose of said radiation upon receiving said radiation from said radiation generating apparatus, for detecting a radiation image by receiving radiation transmitted through an object, a radiation detector for outputting a detection signal according to said radiation dose, in order to detect an emission start of said radiation from said radiation generating apparatus, and/or in order to measure a total radiation dose of said radiation, and a communication interface for communicating with said radiation generating apparatus, said control method comprising steps of:
selectively setting one of first and second operating modes;
wherein said first operating mode is used in case of combination with said radiation generating apparatus with which said communication interface has communication compatibility, for performing at least an exposure control for measuring said total radiation dose according to said detection signal from said radiation detector;
said second operating mode is used in case of combination with said radiation generating apparatus with which said communication interface has communication incompatibility, for performing at least a control of start synchronization for detecting said emission start according to said detection signal from said radiation detector and starting a storage step of storing said signal charge of said image detector in synchronism with said emission start;
controlling said image detector and said radiation detector according to said one operating mode selectively set by said mode setting step.

* * * * *